United States Patent
Adelman

(10) Patent No.: US 11,747,322 B2
(45) Date of Patent: Sep. 5, 2023

(54) MODULAR HAND-HELD POINT OF CARE TESTING SYSTEM

(71) Applicant: iAssay, Inc., San Diego, CA (US)

(72) Inventor: Lonnie W. Adelman, San Diego, CA (US)

(73) Assignee: iAssay, Inc., San Diego, CA (US)

( * ) Notice: Subject to any disclaimer, the term of this patent is extended or adjusted under 35 U.S.C. 154(b) by 0 days.

(21) Appl. No.: 17/734,020

(22) Filed: Apr. 30, 2022

(65) Prior Publication Data

US 2022/0268758 A1 Aug. 25, 2022

Related U.S. Application Data

(63) Continuation of application No. 17/001,069, filed on Aug. 24, 2020, now Pat. No. 11,320,418, which is a
(Continued)

(51) Int. Cl.
*H04W 4/80* (2018.01)
*G01N 21/25* (2006.01)
(Continued)

(52) U.S. Cl.
CPC ... *G01N 33/48785* (2013.01); *A61B 5/02055* (2013.01); *G01N 21/25* (2013.01);
(Continued)

(58) Field of Classification Search
CPC .................. G01N 33/53; G01N 33/48; G01N 2021/7786; G01N 21/6486; A61B 2560/0406
See application file for complete search history.

(56) References Cited

U.S. PATENT DOCUMENTS 5,798,273 A  8/1998 Shuler et al.
6,503,555 B1  1/2003 Katta et al.
(Continued)

FOREIGN PATENT DOCUMENTS

EP  1147739 A2  10/2001
EP  1403795 A1  3/2004
(Continued)

OTHER PUBLICATIONS

GuruBrew, "How to Replace DVD/CD Drive in Computer Tower", https://www.youtube.com/watch?v=27bFqWrx0Ss, Nov. 12, 2012 (Year: 2012).*
(Continued)

*Primary Examiner* — Maurice C Smith
(74) *Attorney, Agent, or Firm* — Wagenknecht IP Law Group PC

(57) ABSTRACT

A modular hand-held point of care testing system, which includes a plurality of different assay adapters configured to receive a plurality of different assay devices that perform assays on one or more samples; a shared door that that interchangeably receives the plurality of different assay adapters; wherein at least two of the plurality of assay adapters or at least two of the assay devices comprise different identifiers that distinguish the assays from each other; an apparatus comprising a portable frame configured to interchangeably receive the shared door and a means for decoding the different identifiers when received by the frame; and a means for reading assay results.

13 Claims, 15 Drawing Sheets

Related U.S. Application Data continuation-in-part of application No. 16/380,861, filed on Apr. 10, 2019, now Pat. No. 10,753,921, which is a continuation of application No. 14/651,167, filed as application No. PCT/US2013/074209 on Dec. 10, 2013, now Pat. No. 10,309,954.

(60) Provisional application No. 63/012,228, filed on Apr. 19, 2020, provisional application No. 62/908,477, filed on Sep. 30, 2019, provisional application No. 61/797,691, filed on Dec. 12, 2012.

(51) Int. Cl.

| | | |
|---|---|---|
| *G01N 33/487* | (2006.01) | |
| *H04W 12/02* | (2009.01) | |
| *H04W 12/033* | (2021.01) | |
| *A61B 5/0205* | (2006.01) | |
| *G01N 21/64* | (2006.01) | |
| *G01N 33/497* | (2006.01) | |
| *H04W 12/08* | (2021.01) | |
| *H04W 88/06* | (2009.01) | |
| *A61B 5/00* | (2006.01) | |
| *A61B 5/01* | (2006.01) | |
| *A61B 5/021* | (2006.01) | |
| *A61B 5/024* | (2006.01) | |
| *A61B 5/08* | (2006.01) | |
| *A61B 5/1455* | (2006.01) | |

(52) U.S. Cl.
CPC ....... *G01N 21/6486* (2013.01); *G01N 33/487* (2013.01); *G01N 33/497* (2013.01); *H04W 4/80* (2018.02); *H04W 12/02* (2013.01); *H04W 12/033* (2021.01); *H04W 12/08* (2013.01); *A61B 5/0059* (2013.01); *A61B 5/0071* (2013.01); *A61B 5/01* (2013.01); *A61B 5/021* (2013.01); *A61B 5/02438* (2013.01); *A61B 5/0816* (2013.01); *A61B 5/1455* (2013.01); *A61B 5/6898* (2013.01); *H04W 88/06* (2013.01)

(56) References Cited

U.S. PATENT DOCUMENTS

| | | |
|---|---|---|
| 6,699,188 B2 | 3/2004 | Wessel |
| 8,172,761 B1 | 5/2012 | Rulkov et al. |
| 8,333,717 B1 | 12/2012 | Shaanon et al. |
| 8,675,356 B2 | 3/2014 | Strauser |
| 9,425,651 B2 | 8/2016 | Strauser |
| 9,685,803 B2 | 6/2017 | Strauser |
| 9,903,857 B2 | 2/2018 | Polwart et al. |
| 10,309,954 B2 | 6/2019 | Adelman et al. |
| 10,753,921 B2 | 8/2020 | Adelman et al. |
| 11,320,418 B2 | 5/2022 | Adelman |
| 2003/0141358 A1 | 7/2003 | Hudson et al. |
| 2005/0137481 A1 | 6/2005 | Sheard et al. |
| 2005/0203353 A1 | 9/2005 | Ma et al. |
| 2005/0205673 A1 | 9/2005 | Morris et al. |
| 2006/0222567 A1 | 10/2006 | Kloepfer et al. |
| 2007/0071641 A1 | 3/2007 | Brock et al. |
| 2007/0190525 A1 | 8/2007 | Gu et al. |
| 2008/0161661 A1 | 7/2008 | Gizewski |
| 2008/0288178 A1 | 11/2008 | Frazier |
| 2009/0018418 A1 | 1/2009 | Markle et al. |
| 2009/0054741 A1 | 2/2009 | McAleer |
| 2009/0270765 A1 | 10/2009 | Ghesquiere et al. |
| 2009/0282192 A1 | 11/2009 | Maus et al. |
| 2010/0222648 A1 | 9/2010 | Tan |
| 2010/0249965 A1 | 9/2010 | Rao et al. |
| 2010/0267049 A1* | 10/2010 | Rutter .............. G01N 35/00029 435/7.1 |
| 2010/0270149 A1 | 10/2010 | Wang et al. |
| 2010/0305422 A1 | 12/2010 | Say et al. |
| 2010/0309454 A1 | 12/2010 | Zhang |
| 2011/0038765 A1 | 2/2011 | Drucker et al. |
| 2011/0201099 A1 | 8/2011 | Anderson et al. |
| 2012/0095309 A1 | 4/2012 | Price et al. |
| 2012/0113422 A1 | 5/2012 | Kivioja et al. |
| 2012/0123686 A1 | 5/2012 | Xiang et al. |
| 2012/0149035 A1 | 6/2012 | Burd et al. |
| 2012/0308444 A1 | 12/2012 | Zhu |
| 2013/0114203 A1 | 5/2013 | Ignatchenko et al. |
| 2013/0179176 A1 | 7/2013 | Gotthardt |
| 2013/0224767 A1 | 8/2013 | Arai |
| 2014/0242612 A1 | 8/2014 | Wang et al. |
| 2015/0160134 A1* | 6/2015 | Booker ................ G01N 21/278 422/403 |
| 2016/0103075 A1* | 4/2016 | Borich .................. H04W 84/18 422/404 |

FOREIGN PATENT DOCUMENTS

| | | | |
|---|---|---|---|
| WO | 19992236 A1 | 5/1999 | |
| WO | 2010004241 A1 | 1/2010 | |
| WO | WO-2013096817 A2 * | 6/2013 | .......... G01N 21/253 |
| WO | 2014093397 A1 | 6/2014 | |

OTHER PUBLICATIONS

Mudanyali et al. "Integrated Rapid-Diagnostic-Test Reader Platform on a Cellphone," Lab Chip, Aug. 7, 2012, 12 (15):2678-2686.

Hu et al. "DW4IR: A Data Warehouse for Translational Research," Journal of Biomedical Informatics, 2011, 44:1004-1019.

\* cited by examiner

MODULAR HAND-HELD POINT OF CARE TESTING SYSTEM

CROSS REFERENCE TO RELATED APPLICATIONS

This is a continuation of U.S. patent application Ser. No. 17/001,069, filed Aug. 24, 2020, now U.S. Pat. No. 11,320,418, which is a continuation in part of U.S. patent application Ser. No. 16/380,861, filed Apr. 10, 2019, now U.S. Pat. No. 10,753,921, which is a continuation of U.S. patent application Ser. No. 14/651,167, filed Jun. 10, 2015, now U.S. Pat. No. 10,309,954, which is a U.S. national phase application of PCT/US2013/074209, filed Dec. 10, 2013, now expired, which claims benefit of priority to U.S. provisional patent application No. 61/797,691, filed Dec. 12, 2012. Each patent application referred to in this paragraph is herein incorporated by reference in its entirety.

This application also claims benefit of priority to U.S. provisional patent application No. 63/012,228, filed Apr. 19, 2020 and U.S. provisional patent application No. 62/908,477, filed Sep. 30, 2019. Each patent application referred to in this paragraph is herein incorporated by reference in its entirety.

TECHNICAL FIELD

The invention relates to the field of medical devices and more specifically to a handheld point of care system, which includes an apparatus having interchangeable modules, which themselves are configured to conduct a plurality of different assays, and which communicates with external devices to collect additional assay data, displays assay results, and communicates results with remote providers over computer networks.

BACKGROUND OF THE INVENTION

Point of care testing is an important way for healthcare providers to effectively and efficiently provide care to individuals. In particular, point of care testing allows for testing and monitoring of individuals in a plurality of settings including a hospital, clinic, remote reference lab testing facility, doctor's office, home of individual being tested, or anywhere in which an individual may be tested or monitored. Point of care testing, or the carrying out of laboratory tests outside of a traditional laboratory setting, has grown and expanded as a practice over the past 20 years driven at least in part by improvements in technology as well as a marked increase in at-home patient care.

While its use has increased greatly over the past 20 years, point of care testing has long been and remains highly inefficient for both the point of care testing provider as well as the patient. For instance, while it is common for test results to be displayed by portable test devices, such devices do not typically save test data as electronic files that can be transferred or aggregated with other test result data files for subsequent processing or analysis. Rather, test results are usually displayed to the provider, then recorded or inputted manually into patient files or databases, where they can be printed in worksheets for later comparison with other tests.

The inefficiency of point of care testing is also due to the physical cumbersomeness of the point of care testing technology as well as its use. For example, a point of care testing provider, using traditional technology, frequently must utilize either multiple point of care readers, where each reader is configured to perform a single assay or a single reader configured to read more than one assay but only one assay at a time, which itself is selected from a preprogrammed test menu. Thus, conducting tests with different components at the bedside or at a walk-in site conventionally requires multiple readers or at least multiple steps.

However, multiple readers are physically cumbersome to carry from test site to test site and also take up critical bench space at a physician's office, lab or a pharmacy. As a result, a point of care testing provider is typically unable to add additional tests, either ordered by the physician or requested by the patient while they are at the site because the provider does not typically have all testing tools available on hand. Thus, additional testing requires the provider leave and return to the site with the additional testing tools—an obvious source of inefficiency at the point of care.

SUMMARY OF THE INVENTION

The invention addresses the above deficiencies and provides related embodiments. In particular, described herein are hand-held modular point of care testing systems and methods for testing individuals, which permit multiple tests to be performed using a single handheld apparatus. Moreover, the systems and methods also permit receiving test results or data from other testing devices or systems, and securely pairing, analyzing and/or communicating test result files.

The systems and methods described herein are efficient in numerous ways including how assay results and data are collected from multiple data sources; and how results and data are transmitted to a network or networks and/or server or servers that are accessible to healthcare providers and laboratory personnel. In addition, the systems and methods address a long felt but unmet need with respect to traditional point of care testing technology for reducing the cumbersomeness and inefficiency in existing technology in that the instant systems and methods, for example: (1) efficiently collect and transmit data from multiple different types of input sources; and (2) provide multiplex analysis for multiple different assays and sample types.

The above is accomplished in one aspect of the invention by a modular hand-held point of care testing system, which includes a plurality of assay modules configured to receive different assay devices to perform assays on one or more samples, such as a biological sample or environmental sample, and where at least two of the assay modules or at least two of the assay devices have different identifiers; an apparatus having a portable frame configured to interchangeably receive the plurality of assay modules in a same port; a means for decoding the different identifiers when received by the frame; and a means for reading assay results.

In some embodiments, the assay module is a single component that is inserted into the frame of the assay device; however, in preferred embodiments the assay module includes an assay adapter configured to receive the assay device and a door that receives the adapter. In further embodiments, the door is shared between different assay adapters for different assay devices.

In some embodiments, at a distal end of the assay adapter can be a slot positioned transverse to the longitudinal extent of the assay module and a movable flap configured to reversibly cover the slot and extend parallel to the longitudinal extent of the assay module.

In some embodiments, at a proximal end of the door can be a handle, optionally configured as a proximal knob, for removing the assay module from the frame, and at a distal end of the assay adapter can be distal fingers slots for removing the assay adapter from the door.

Preferably, the apparatus is configured for multiplex testing by conducting a plurality of tests. In some embodiments, the apparatus reads test results from a plurality of assays conducted on a single test device. In other embodiments, the apparatus reads test results from a plurality of assays conducted on two or more test devices. In some embodiments, the apparatus receives more than one assay module or assay device, thereby performing more than one assay. In some embodiments, two or more assays are performed simultaneously. Nonlimiting examples of assays that can be performed include one or more assay selected from the group consisting of a Sodium assay, Potassium assay, Chloride assay, BUN/Urea assay, Glucose assay, Hematocrit assay, Ionized Calcium assay, P02 assay, pH assay, PC02 assay, Creatinine assay, Lactate assay, Celite ACT assay, Prothrombin Time PT/INR assay, Kaolin ACT assay, Cardiac Troponin I/cTnl assay, Total Carbon Dioxide/TC02 assay, Creatine Kinase MB/CK-MB assay, B-Type Natriuretic Peptide/BNP assay, an immunodiagnostic assay, a DNA sequencing assay, a bioluminescent assay, a cell cytometry assay, a lateral flow assay, and an HbA1c assay.

In some embodiments, at least one assay is an immunodiagnostic assay, optionally an enzyme-linked immunosorbent assay (ELISA). In some embodiments at least one assay is a lateral flow immunoassay, which optionally includes analysis of line presence or absence, intensity, line color, or a combination thereof. At least one assay can be a DNA sequencing assay based on DNA sequencing chip(s). At least one assay can include polymerase chain reaction (PCR). At least one assay can be a microfluidic assay. At least one assay can detect or measure in a change in electric charge or pH, such as to detect or measure cell growth or metabolism.

In some embodiments at least one assay device includes an immunoassay test strip. The assay device can be a cartridge or container. The assay device can be a closed container with an electronic interface that uses nanoparticle technology internally to perform the assay. In some embodiments the assay device includes an image capture device and LCD display, which can be inserted into the apparatus and the image captured. Optical character recognition software can then identify the text or other identifying indicia to automatically identify the assay so that any required settings or programming can be initiated or followed and/or so that a graphical user interface is populated with proper control option or display.

Identifiers can be used to distinguish one assay from another. In some embodiments, the identifier is on the assay device itself (e.g. manufacturer's printed information); and in other embodiments, the identifier is on the assay module. In some embodiments the identifiers include indicia, such as, but not limited to a bar code, a QR code, an alphanumeric code, and a color code and where the means for decoding the indicia includes an indicia reader (e.g. bar code, QR code, alphanumeric code and/or color code reader). In other embodiments, the identifiers include an RF tag or NFC circuit, and the means for decoding the RF tag or NFC circuit includes an RF tag reader or NFC reader. In other embodiments, the identifier includes structural features that distinguish the assay device from others, which can be decoded using optical imaging or optical scattering analysis in conjunction with optical character recognition software. In some embodiments, the identifiers include differently ordered teeth, and the means for decoding the differently ordered teeth includes a photointerrupter. Control teeth may also be provided to confirm proper insertion of the assay into the frame.

In some embodiments, the apparatus includes an imaging module, such as a camera circuit, for optically capturing the identifier and/or assay results. Assay results can then be analyzed using the apparatus. In some embodiments, the apparatus itself has a user interface, microprocessor and memory to read and optionally analyze assay results.

In other embodiments, the portable frame has a keeper adapted to receive and keep a smart device (e.g. smartphone or tablet computer) or independent touch screen. In embodiments including a smart device (e.g. smartphone or tablet computer) or embodiments that functionally connected to a smart device, the invention can also include downloadable software for the smart device for reading and/or analyzing assay results. In some embodiments, the portable frame is adapted to receive (or the portable apparatus includes) one or more single board computers, such as but not limited to a Raspberry Pi, optionally running Linux.

In some embodiments, the apparatus or smart device includes optical stabilization software for stabilizing optical reading or results. In other embodiments the system includes a stabilization structure, optionally configured as a gimbal, that improves stability of the apparatus, assay module and/or or assay device during shock or movement. In some embodiments, stabilization is accomplished electronically via a gravitational sensor that simultaneously sends position data to the apparatus so that image shaking can be corrected. In related embodiments, the stabilization is accomplished optically and/or electronically, such as by detecting positioning or movement of one or move bubble levelers or colored liquids/polymers that shift when moved in one or more directions, then adjusting for the movement.

In some embodiments, the apparatus includes a collimator. In some embodiments, the apparatus includes one or more of a light pipe, lens, prism, signal guiding, or amplification device lined-up with a camera, imaging modalities, or detection device.

In some embodiments, the means for reading assay results includes a luminescence recorder adapted to record luminescence. Nonlimiting examples of luminescence recorders include a camera, a fluorescent light recorder, a UV recorder, a diode/amplifier type receiver, and a combination thereof. In some embodiments, the luminescence recorder is a built-in camera of a portable computing device.

The system can also include a bright field light source (e.g. white light) and/or an excitation light source configured to deliver a wavelength to the assay device that excites fluorescent molecules and a fluorescence detector for detecting fluorescence. In some embodiments, the light source is positioned on the assay module. In other embodiments, the light source is positioned within the portable frame. Non-limiting examples of light sources include one or more laser diodes or light emitting diodes (LEDs), optionally selected from the group consisting of white light, an ultraviolet light, a violet light, a blue light, a green light, a yellow light, an orange light, and a red light. Lighting can be controlled by independent circuit boards, device processor or smart device.

In some embodiments the system is configured to conduct or communicate with a vital sign detector configured to sense one or more vital signs of an individual. Non limiting examples include stethoscopes, blood pressure cuffs, and heart rate monitors. The system can also communicate with biological sensors including insulin sensors. Communication can be one-way or two-way, and thus the system can include suitable ports, such as USB ports or a transceiver configured to transmit and receive data. The transceiver can operate on one or more transmission technologies, including but not limited to 3G communication protocols, 4G communication protocols, 5G communication protocols GSM standards, CDMA protocols, IEEE 802.11 standards, Bluetooth protocols, Wifi protocols, and satellite communications. Communication can be by visible light communications, infrared communications, a hardwired connection, or near field communication. In some embodiments, the system communicates with other assays devices.

In some embodiments, the system includes a universal interoperability coupler for coupling different assay modules to a same port. The universal operability coupler can include adjustment bars with external handles that allow the user to preset the external handles to positions that hold the assay module in place.

The system can also include a functional module that performs an electrical operation to supplement the testing system. Preferably, the functional module is configured for interchangeable insertion into the same port as the plurality of assay modules. In some embodiments, the system includes a universal interoperability coupler for coupling different functional modules to a same port as assay modules. In some embodiments, the assay modules and functional modules share similar dimensions for interchangeable connection within a same port of the apparatus.

In some embodiments, the functional module includes a transceiver. In some embodiments, one or more functional modules include one or more of a battery, a wireless data transmission device, a wired data transmission device, a microprocessor, an interface for receiving and recording signals from at least one vital sign detector, a luminescence recorder, a display device, a portable computing device, a data storage device, and a hub for electrically connecting one or more assay modules to the apparatus.

In some embodiments, the functional module includes a wireless data transmission device, optionally operating on one or more transmission technologies, including of 3G communication protocols, 4G communication protocols, 5G communication protocols, GSM standards, CDMA protocols, IEEE 802.11 standards, Bluetooth protocols, satellite communications, visible light communications, infrared communications, and near field communications. In some embodiments the functional module transmits data to a local area network or the Internet. In some embodiments, the functional module includes an adapter for powering an external device (e.g. powered USB).

In view of the above, also disclosed is a modular hand-held point of care testing system, which includes an assay module configured to receive an assay device to perform an assay on a biologic sample; a functional module that performs an electrical operation to supplement the testing system; and an apparatus with portable frame having a plurality of ports, where at least two ports are each configured to interchangeably receive the assay module and the functional module, and where, the apparatus includes or is configured to functionally connect to a means for reading assay results.

Also in view of the above, a modular point of care testing system is provided, which includes an assay module configured to receive an assay device that performs an assay on a sample, such as a biological or environmental sample, alone or in combination with the assay module; an apparatus with portable frame configured to receive the assay module and read assay results from the assay device; a transmitter configured to transmit data from the assay module or apparatus to a mobile computing device or a remote server; and a universal interoperability coupler configured to operably couple a plurality of different assay modules and optionally functional modules with the portable frame.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
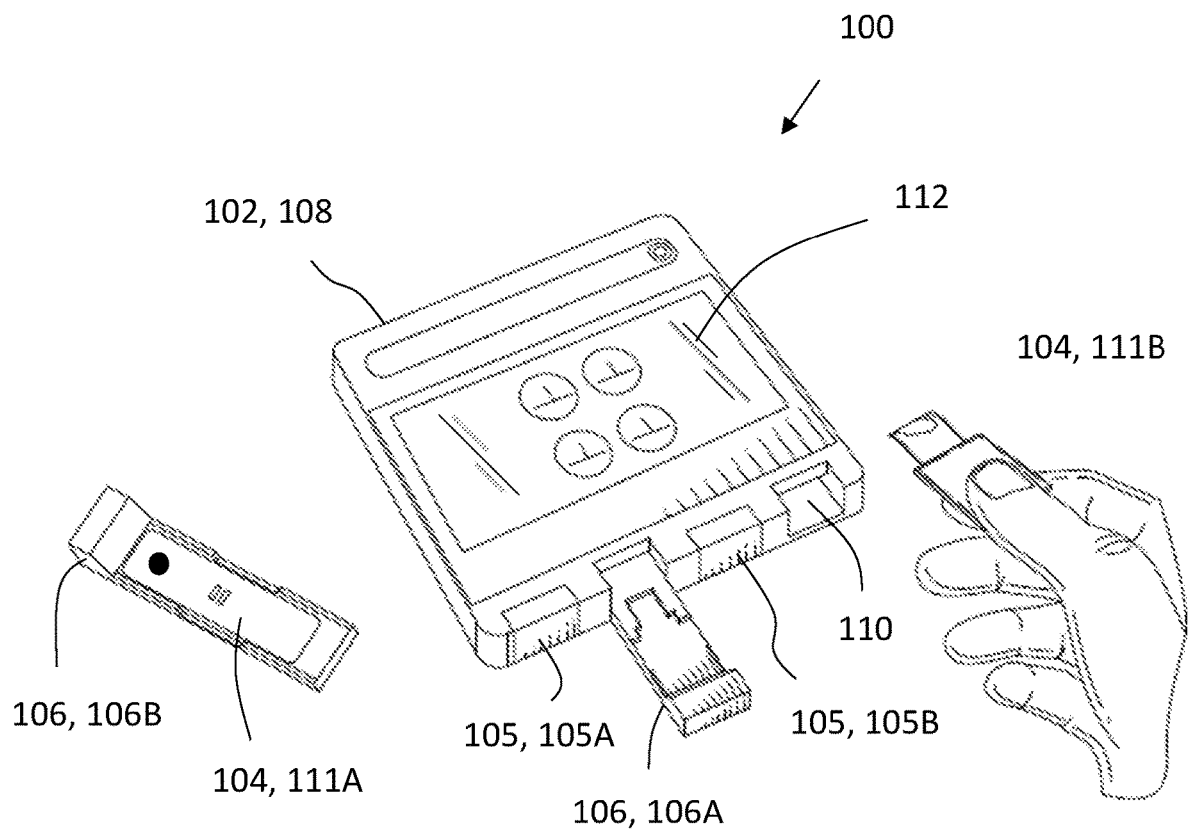
FIG. 1 shows an exemplary embodiment of a modular hand-held point of care testing system 100, showing an exemplary apparatus 102 receiving functional modules 105A, 105B and assay modules 106A, 106B and having a graphical user interface 112 for displaying and instructing transmission of data files.

The present disclosure is described in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate preferred embodiments of the invention, and not to exhaustively specify all permutations, combinations and variations thereof.

As an introduction, described herein are modular handheld point of care testing and monitoring systems configured to carry out tests and measurements including, but not limited to, biologic sample testing and physical parameter (e.g. vital sign) measurement. Assays performed by the systems generally include healthcare assays and veterinary assays for detecting and monitoring medical conditions of individuals but can also be adapted for food product assays and environmental assays.

As used herein, the term "point of care" means any location where a hand-held testing system may be utilized and/or any location at which healthcare may be delivered to an individual. Non-limiting examples of a point of care includes a home of a patient, a health clinic or doctor's office, a mobile clinic or other field clinic site, a nursing home, a rehabilitation facility, or hospital.

As used herein "biologic sample" or "biological sample" means a sample obtained from an individual. Examples include bodily fluids such as blood, serum, plasma, saliva, urine, ocular fluid, semen, and spinal fluid. Samples can be suspensions made from solid, semi-solid or highly viscous materials, such as soils, fecal matter, tissues, organs or other samples that are not fluid in nature. For example, these solid or semi-solid samples can be mixed with an appropriate solution, such as a buffer (e.g. a diluent or extraction buffer). The sample can be macerated, frozen and thawed, or otherwise extracted to form a fluid sample or suspension sample. Residual particulates can be removed or reduced using conventional methods, such as filtration or centrifugation. "Biological samples" can include cells, microbes, organdies, nucleic acids (DNA, RNA), polypeptides, analytes, and biochemical complexes. As used herein, the term "individual" means any human or animal.

The term "environmental sample" means a specimen taken from surroundings such as water, soil, municipal waste, hazardous waste, potential pollutants and others. Environmental samples can be used to assess water quality, soil quality, air quality, pollution, ecology, fisheries, forestry and other environmental studies. In some embodiments, environmental assays test for the presence or abundance of one or more inorganic compound or metal.

Turning now to FIG. 1, a modular hand-held point of care testing system 100 is depicted, which is configured to run a variety of laboratory tests on one or more biologic samples. More specifically, system 100 includes apparatus 102, which is configured to read test results from a plurality of different assay devices 104. Jumping briefly to FIG. 10, test results can then be communicated to the operator or can be transmitted over a computer network 510 for remote analysis and monitoring.

Figure 2A:
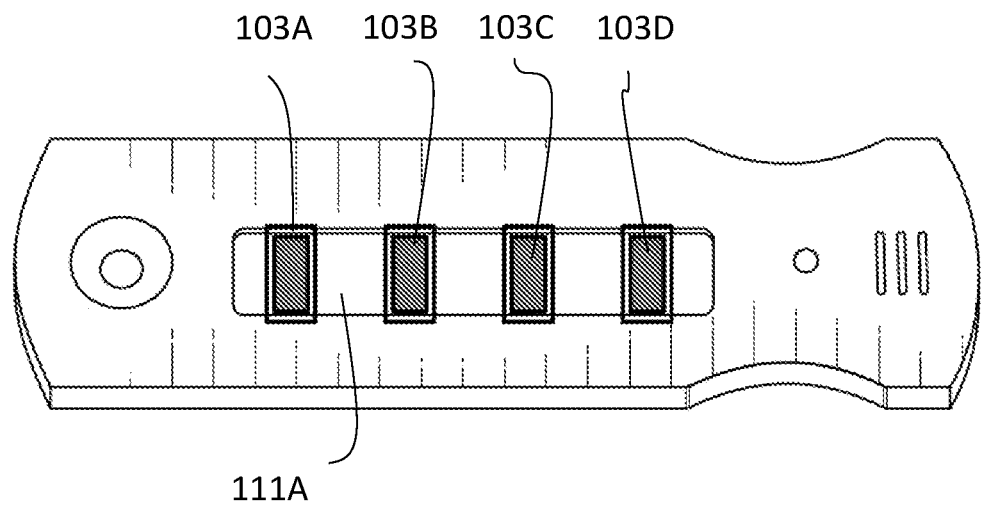
FIG. 2A is an exemplary lateral flow test device 104 for use with the invention that is configured to test for four different analytes 103A-103D on a single test strip 111A.
Figure 2B:
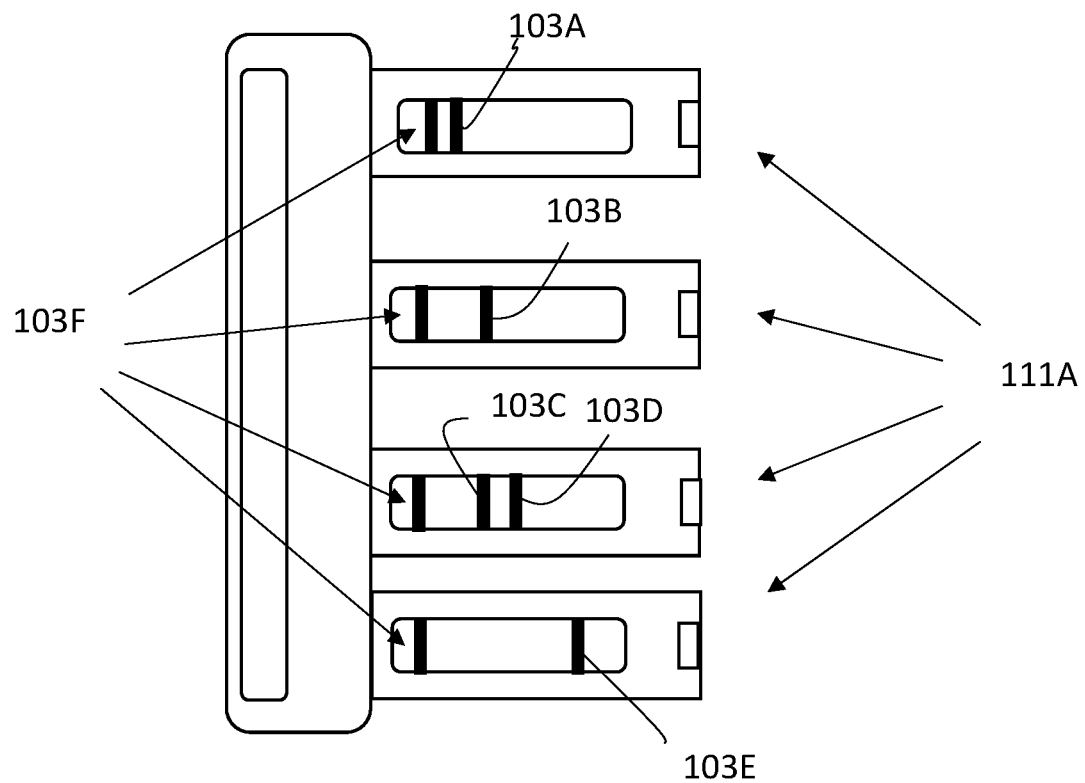
FIG. 2B is another exemplary lateral flow test device 104, which tests for five analytes 103A-103E (and control 103F) on separate test strips 111A.
Figure 2C:
FIG. 2C is a test device 104 in the form of a container 105 having electrodes 119A, 119B for measuring electric properties of the sample (119A) and electric properties of a solution (119B) within which the sample is incubated.
Figure 3A:
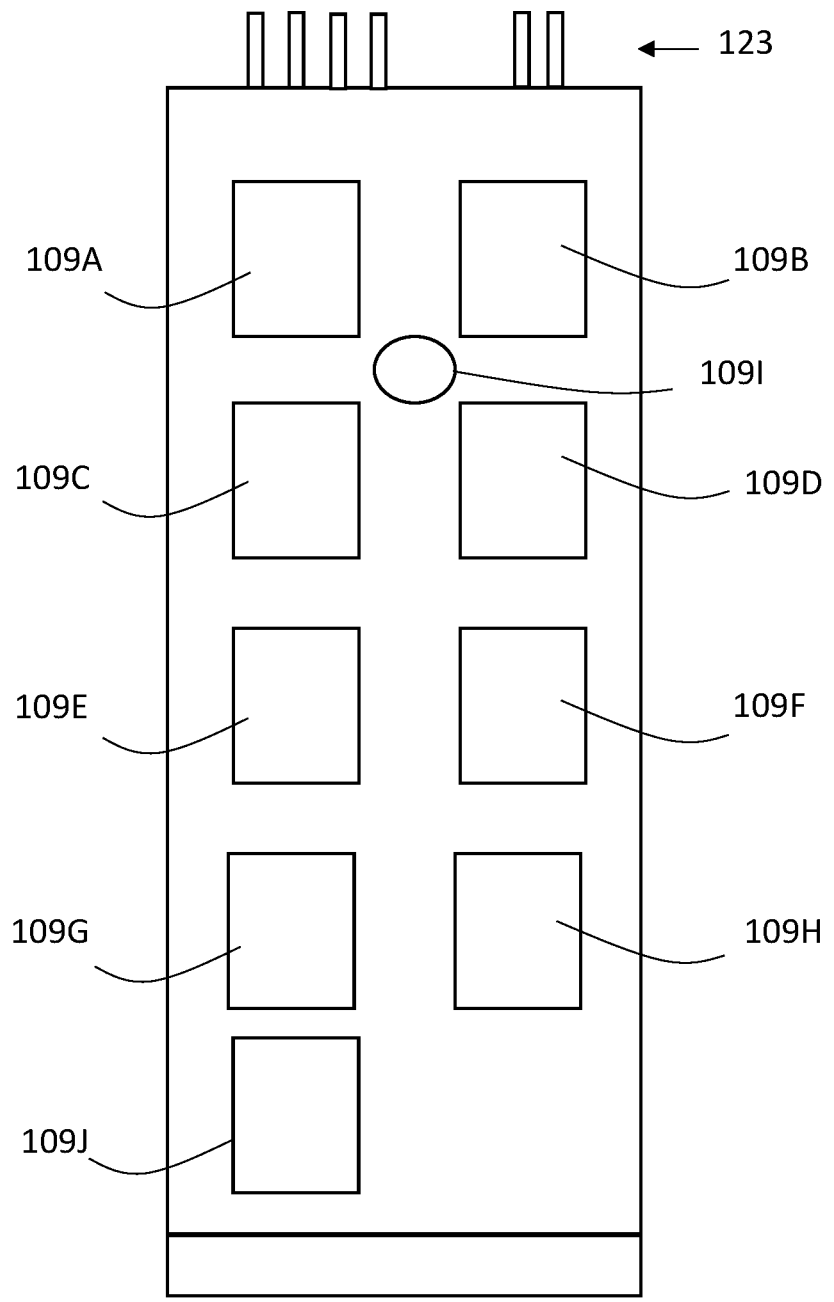
FIG. 3A is a schematic of an exemplary multipurpose functional device 105.
Figure 3B:
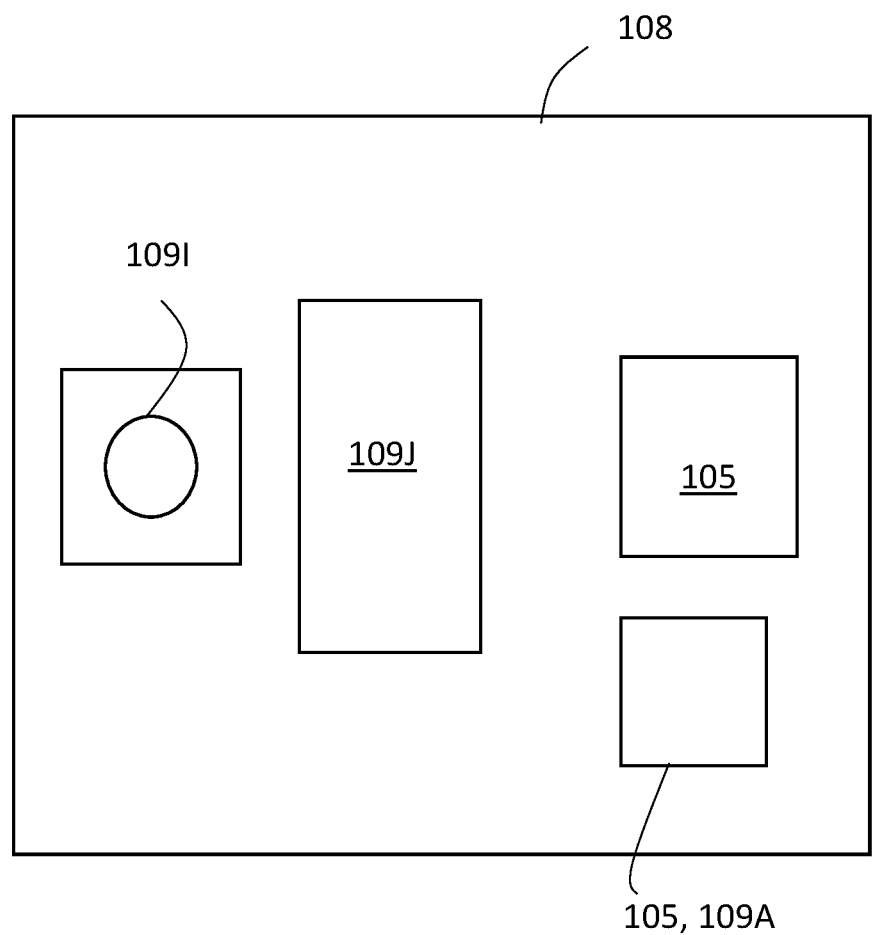
FIG. 3B is a schematic of an exemplary apparatus 102 showing an integrated camera 109I and single board computer 109J.

Moving on to FIGS. 2A-2C, which will be described in more detail in passages that follow, assay device 104 is a structure upon or within which a biological assay is performed. To this end, assay device 104 can include any suitable container 105 or receptacle for receiving and holding a sample during testing. Thus, a container 105 refers to an assay device 104 having a receptacle for receiving and holding a sample during testing.

In some embodiments, the biological assay can be conducted solely using the assay device 104, such as where all components of the assay are positioned in or on assay device 104. An example is shown in FIG. 2A, where test device 104 includes a test strip 111A that conducts a lateral flow assay able to capture and thus display the presence or abundance of different analytes 103A-103D using antibody capture techniques known in the immunodiagnostic arts. FIG. 2B depicts a similar configuration, where a single test device 104 includes four separate test strips 111A configured to detect or measure five analytes 103A-103E plus control 103F. However, as depicted in FIG. 2C, in other embodiments the assay is conducted within assay device 104 but requires further input from apparatus 102 such as delivering electricity to electrodes 119A-119B via electric contacts 129 or by inducing fluorescence using LEDs 113F positioned within apparatus 102 (see FIG. 8).

Turning now to FIGS. 1-10 collectively, assay device 104 is preferably held using assay module 106, which itself is configured for insertion into portable frame 108 of apparatus 102. That is, assay module 106 is adapted for coupling assay device 104 with portable frame 108 so that apparatus 102 can read assay results from assay device 104. As nonlimiting examples, assay module 106 may be configured to couple with assay devices 104 embodied as a sample container 105 (e.g. a cartridge, housing, or cuvette 111B) or a test strip 111A lacking a surrounding cartridge or housing. In embodiments where assay module 106 receives assay device 104 configured as a sample container 105, assay module 106 can electronically couple assay device 104 to apparatus 102 such as using suitable electronic connectors and circuitry for conducting an assay within the container (e.g. to provide power to an electrode-based assay). Likewise, assay module 106 may be configured as an interface to transfer data (e.g. electrical test data) from assay device 104 to apparatus 102. Moreover, as best seen in FIG. 1, apparatus 102 can conduct different tests simultaneously, which can be monitored using graphical user interface 112. In particular, assay module 106A is shown ready for receiving cuvette 111B for insertion into apparatus 102 for conducting a first test, and assay module 106B is shown with test strip 111A ready for insertion into available port 110 of apparatus 102 to conduct a second test on a same sample. Test results are then communicated or transmitted through a network to healthcare providers.

FIG. 1 also shows apparatus 102 with two already received functional modules 105A, 105B, which are sized to share a same port 110 as assay modules 106A, 106B within frame 108. Functional module 105 is a component that performs an operation to supplement or assist apparatus 102 but does not itself conduct a biological assay nor does it physically receive an assay device 104 for insertion into frame 108 for reading assay results. Functional module 105 may however, receive assay results from another device (e.g. thermometer, pulse and blood oxygen monitor) for pairing with patient data. Moving on to FIG. 3A, a functional module 105 can be or can include one or more of: a battery 109A, a wired or wireless data transmission device 109B, a microprocessor 109C, an interface for receiving and recording signals from at least one vital sign detector 109D, a luminescence recorder 109E, a display device 109F, a portable computing device 109G, a data storage device 109H, a camera 109I, and others. In some embodiments functional module 105 receives data from a third-party assay for pairing with patient data obtained by apparatus 102, then communicates or transmits paired data to healthcare providers.

In view of the above, one of the benefits of the system 100 is that it is modular. By "modular" it is meant that the system 100 includes one or more interchangeable components or parts. Typically, two interchangeable modules may be removed and inserted into a same port 110 of the apparatus 102, thereby decreasing the number of required ports 110 to perform multiple assays and functions. Preferably, the system 100 is modular in that two or more assay modules 106 can be interchanged within a same port 110 and two or more functional modules 105 can be interchanged within a same port 110. The system 100 is also preferably modular in that assay modules 106 and functional modules 105 may be interchanged within a same port 110.

Best shown in FIGS. 1, 5A-5C and 9A-9B, apparatus 102 is preferably portable so that system 100 is capability of being operated while being held in the hands of an operator. As such, frame 108 of apparatus 102 is preferably sized and configured to be comfortably held in the hand of a typical user. In some embodiments, frame 108 includes a strap configured to securely or comfortably hold frame 108 within an operator's hand. In addition, frame 108 is primarily formed of generally lightweight polymer components that can be comfortably held and carried when used. Preferably, apparatus 102 is also capable of being operated while being supported by or resting on an inanimate surface, such as on a patient's bed, on a desk or chair, on a utility cart, or any such surfaces located at or close to the site where testing takes place.

Returning collectively to FIGS. 1-10, assay module 106 properly positions assay device 104 in apparatus 102 for reading assay results. As will be explained in more detail in sections that follow, when assay module 106 is inserted into port 110, preferably apparatus 102 identifies the assay so that apparatus 102 initiates required programming to conduct the assay, read assay results, and/or communicate with network 510 (FIG. 10) to receive assay information. As such, assay dependent programming can be identified and started automatically in response to an automated assay identification step. Though not preferred because it is more prone to user error, the artisan will appreciate that a user could also perform one or more steps such as identifying the assay and inputting one or more patient or assay parameters into apparatus 102 using conventional input controls.

Figure 6A:
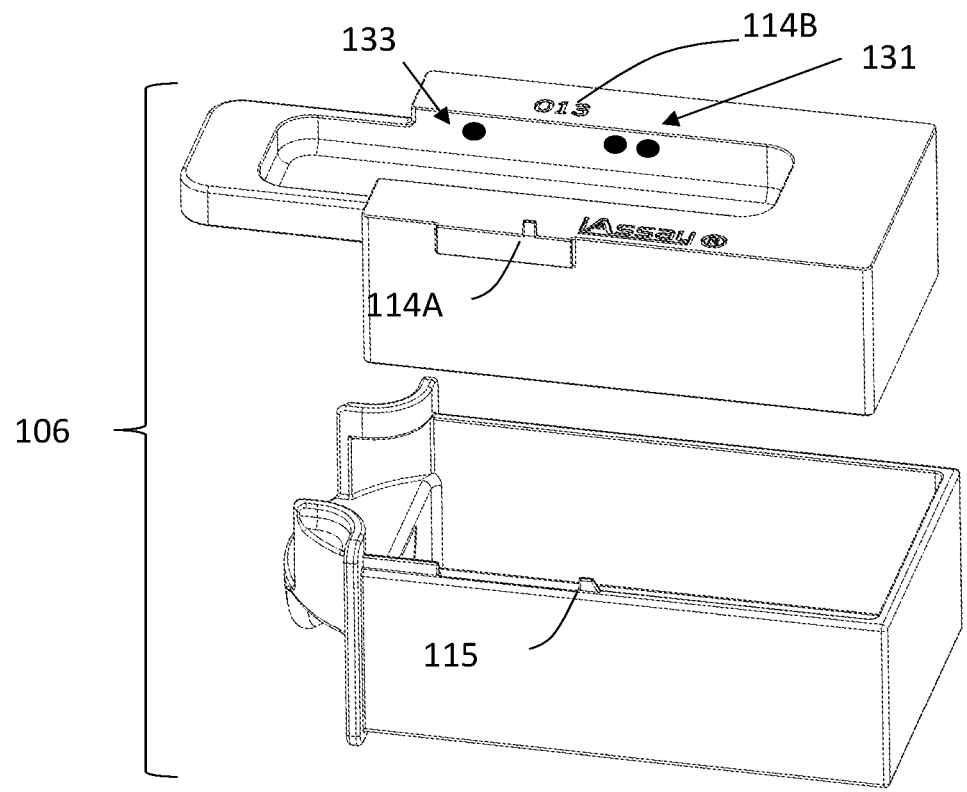
FIGS. 6A-6B depict an exemplary assay module 106 identifiable by teeth 114A and indicia 114B.
Figure 6B:
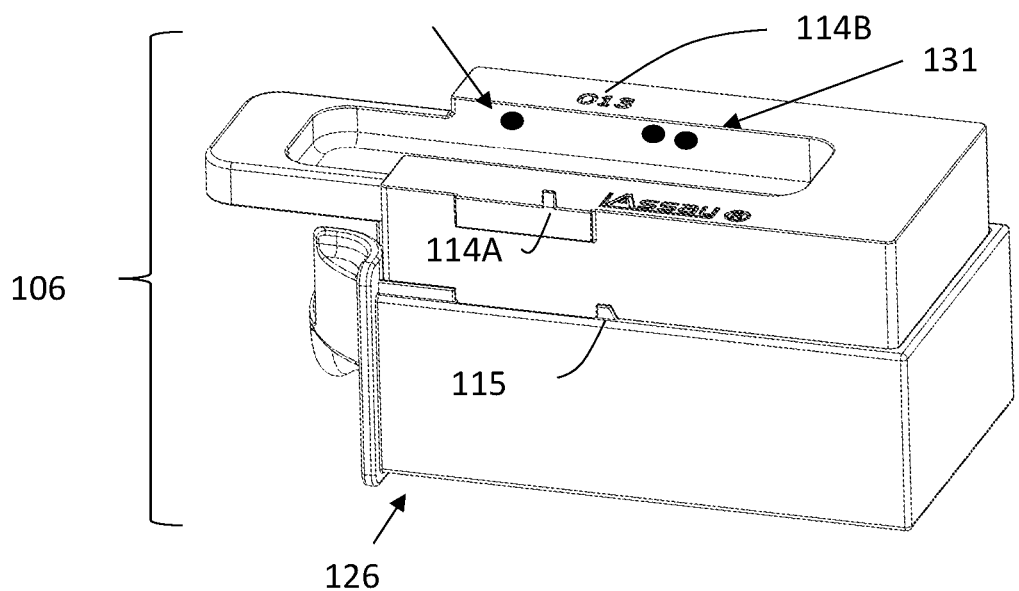
Figure 7:
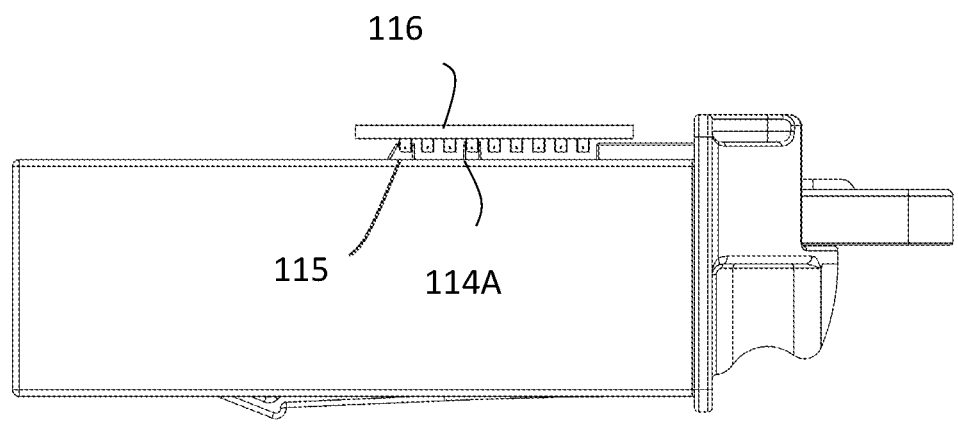
FIG. 7 depicts an exemplary means for automating assay identification.

Moving on to FIGS. 4A-4E, a plurality of different assay modules 106 configured to receive a plurality of different assay devices 104 are depicted. Different manufacturers of assay devices 104 tend to use different sizes and shapes to distinguish their assay devices 104 from others. Thus, conventional assay readers are typically limited to a single assay and its generic copies. One solution to reading different sized assay devices 104 in a single apparatus 102 is to have a plurality of different sized ports 110, which is encompassed by the disclosure herein. Another is to have adjustably sized ports 110, which is also encompassed by the disclosure herein. The solution depicted in FIGS. 4A-5C is the development of a plurality of assay modules 106 that can be interchanged within a same port 110. In particular, each assay module 106 is configured to receive an assay device 104 that performs an assay (e.g. on a biologic sample), and where at least two assay modules 106 and/or at least two assay devices 104 have different identifiers 114. Apparatus 102 is configured to receive each different assay module 106 in a same port 110 and includes a means for decoding identifiers 114 such that when received, identifiers 114 identify the particular assay or assay settings for the apparatus 102 as needed (e.g. qualitative or quantitative assessment), and thus apparatus 102 can initiate programming or setting instructions to perform or read assay results. An example is depicted in FIGS. 6A-7, in which identifiers 114 are embodied as differently ordered teeth 114A. In such embodiments, reading and distinguishing between different assay modules 106 by the apparatus 102 can be by way of a photointerrupter 116 (see FIG. 7) that distinguishes between sets of differently ordered teeth 114A. Also shown is control tooth 115 that ensures assay module 106 is fully inserted into frame 108

A photointerrupter 116 is a photosensor, which typically includes light emitting elements and light receiving elements aligned facing each other in a single package, that work by detecting light blockage when a target object comes between both elements, acting as an optical switch. To this end, different arrays of teeth 114A on different assay modules 106 can be aligned to selectively block different combinations of emitters and receivers for identification. Using this approach, a plurality of assay modules 106 can be adapted to fit in a same port 110; yet be distinguished from one another by the predefined array of teeth 114A. These different arrays of teeth 114A provide the identity of the test device 104 or subgroup of test devices 104 and thus permit the apparatus 102 to automatically proceed with conducting any required steps or adjustments for proper testing or reading.

Figure 4A:
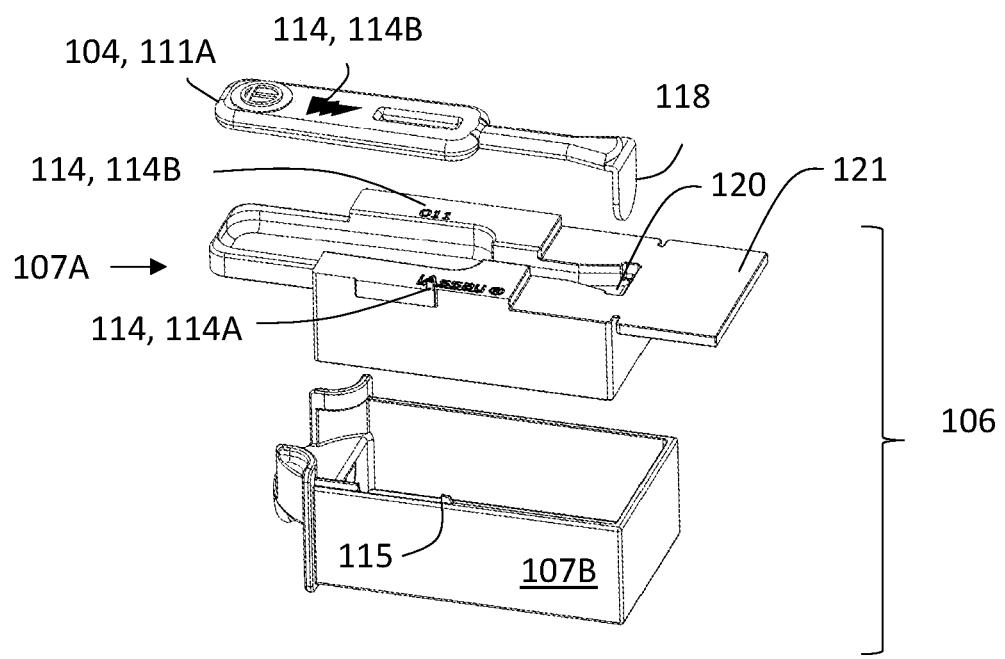
FIGS. 4A-4E show exemplary configurations of various assay devices 104 from different manufacturers being received by assay modules 106, defined generally by different assay adapters 107A that fits into a same door 107B.
Figure 4B:
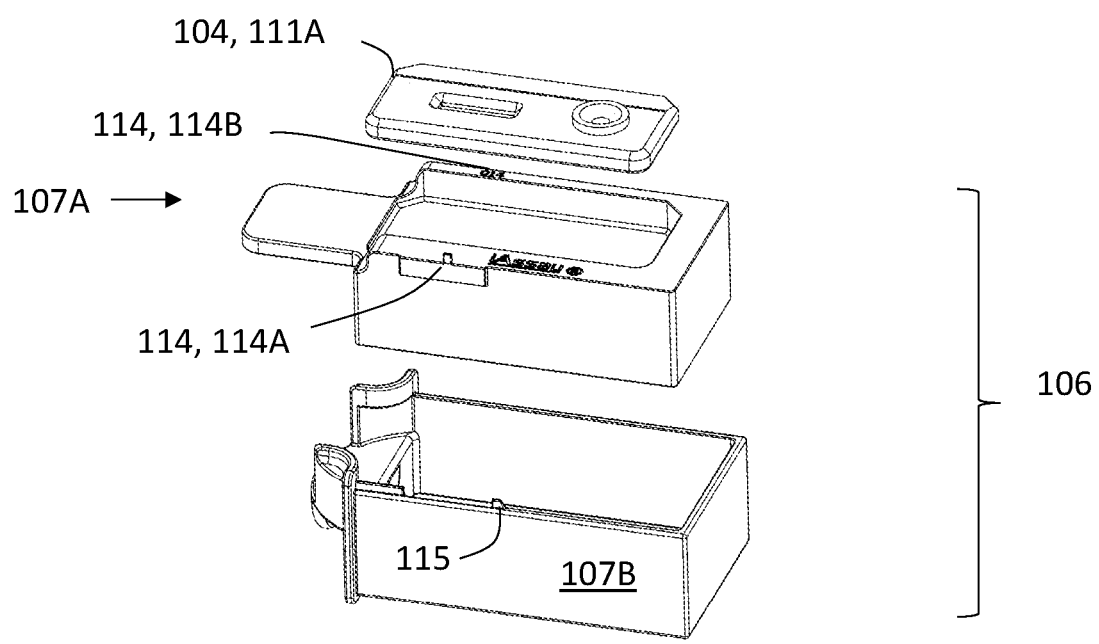
Figure 4C:
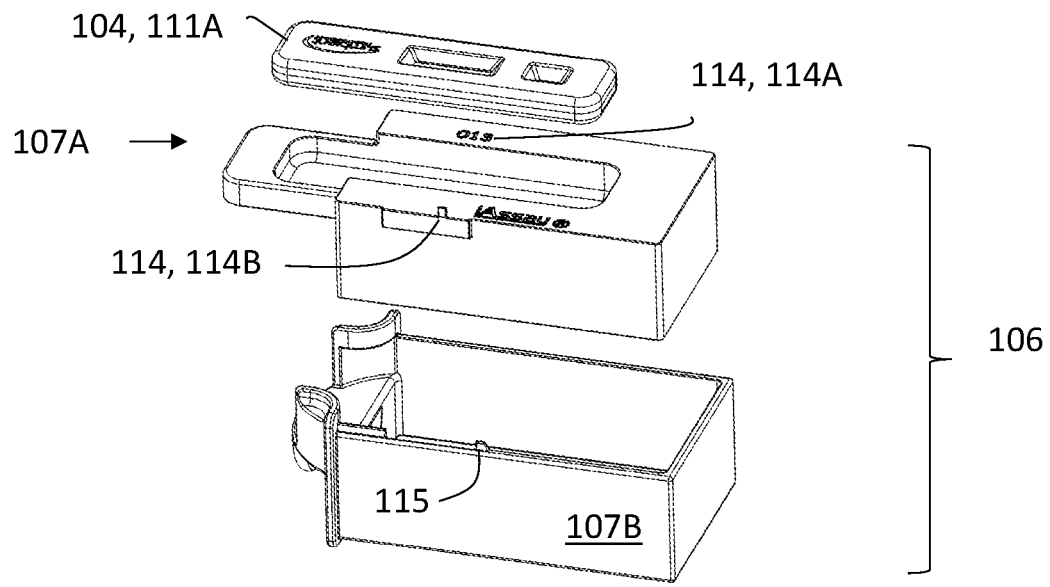
Figure 4D:
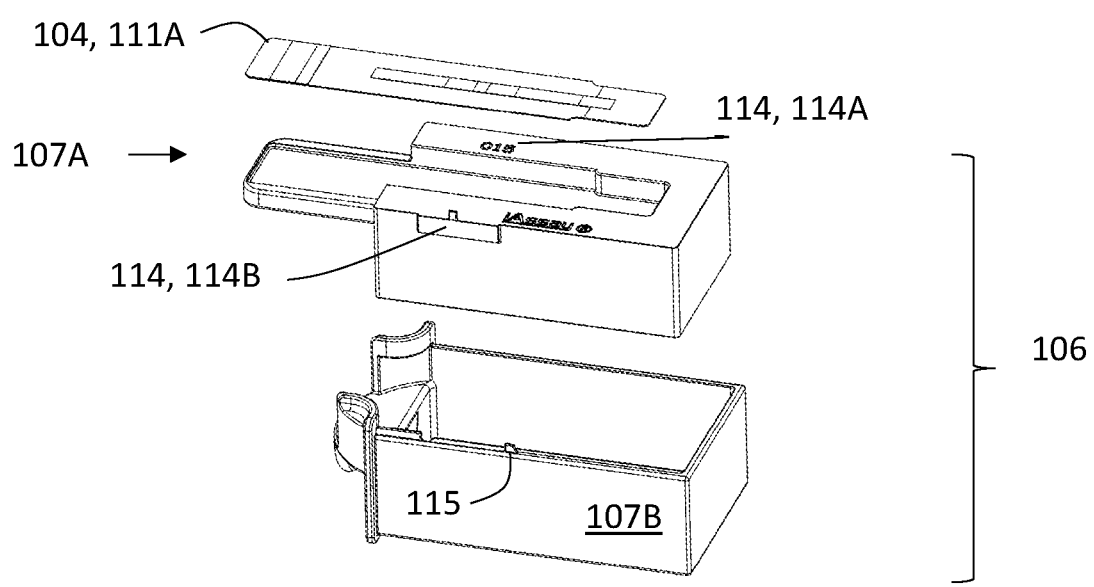
Figure 4E:
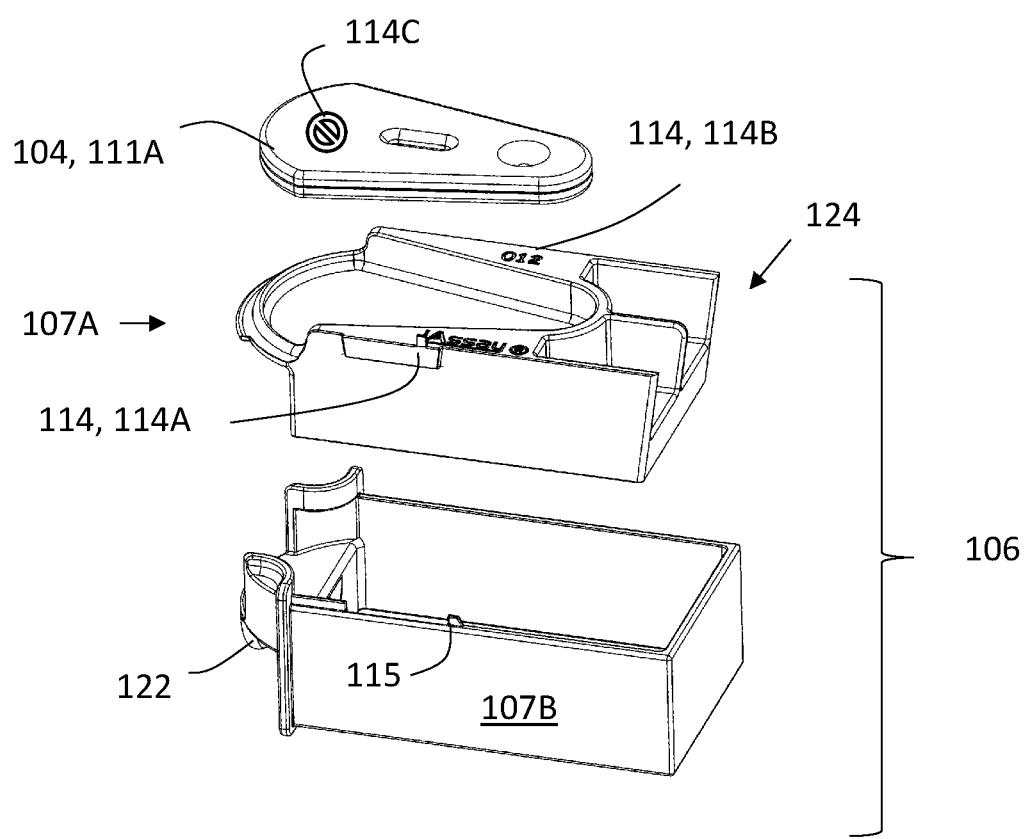
Figure 5A:
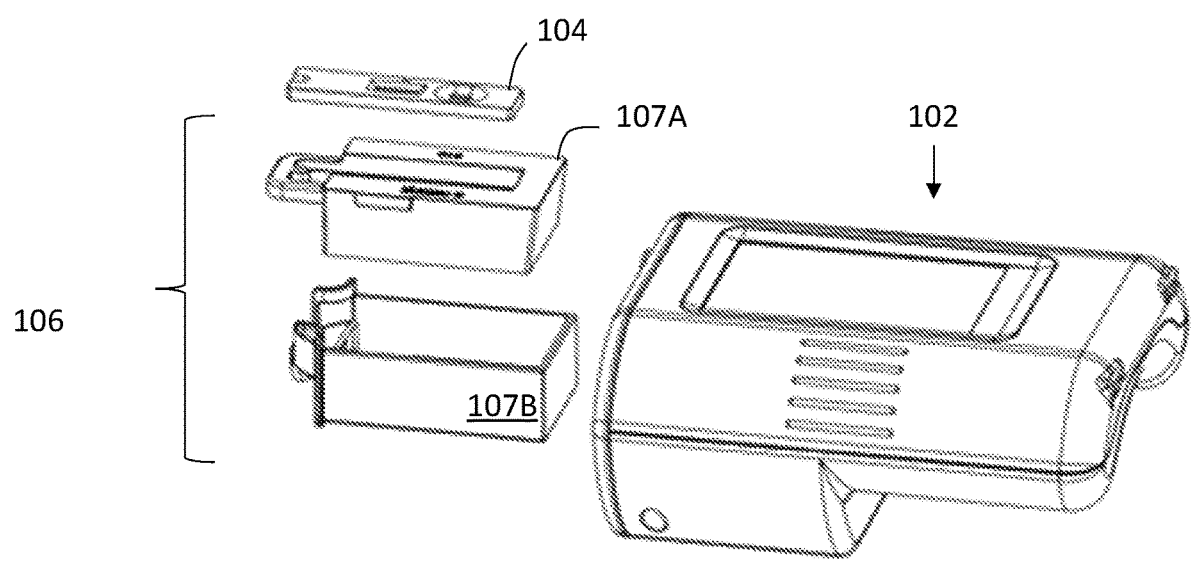
FIGS. 5A-5C show an exemplary method of operation, which includes inserting an assay device 104 into its corresponding assay module 106, then inserting the assay module 106 into the apparatus 102.
Figure 5B:
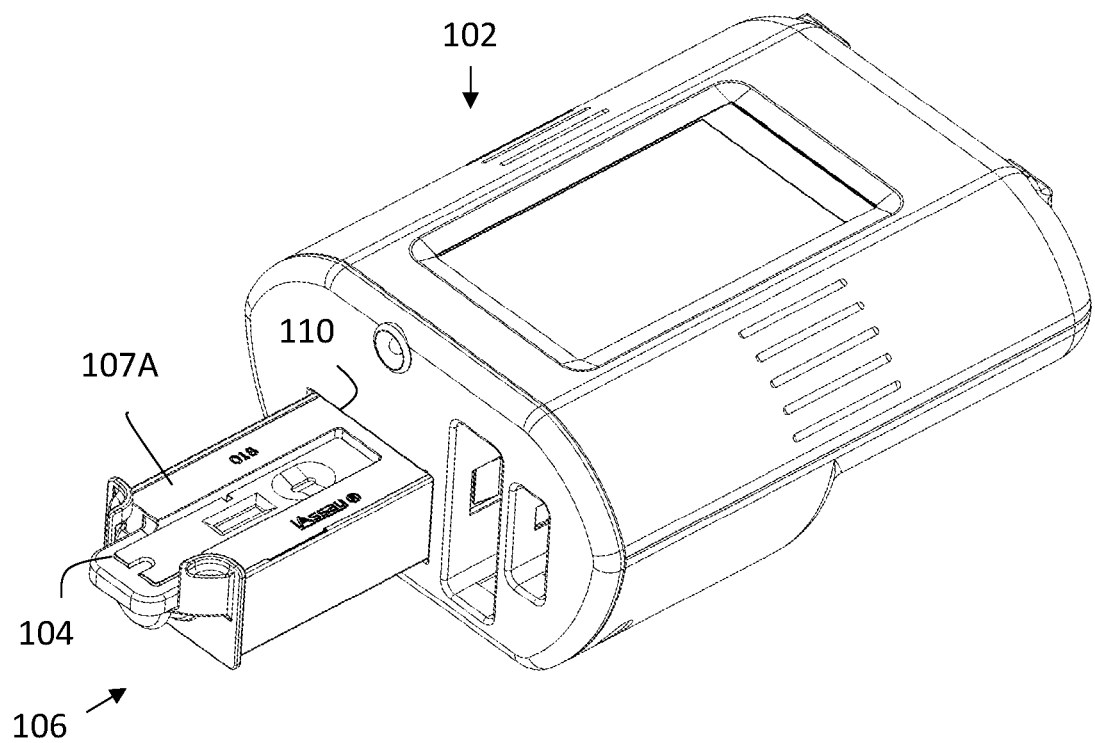
Figure 5C:
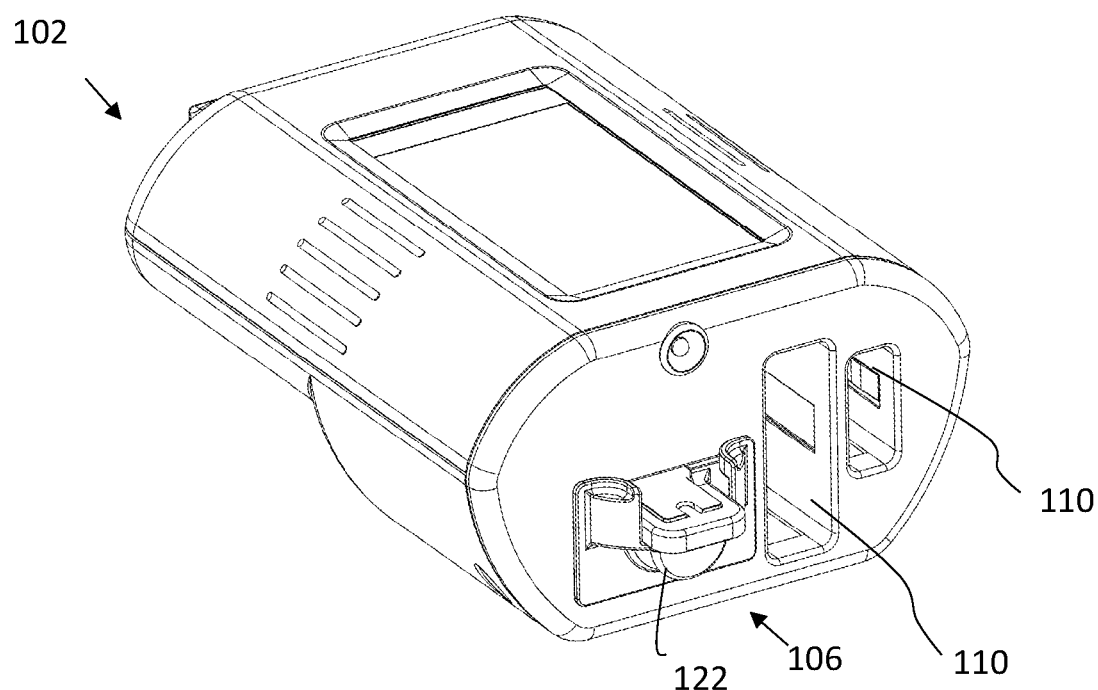
Figure 8:
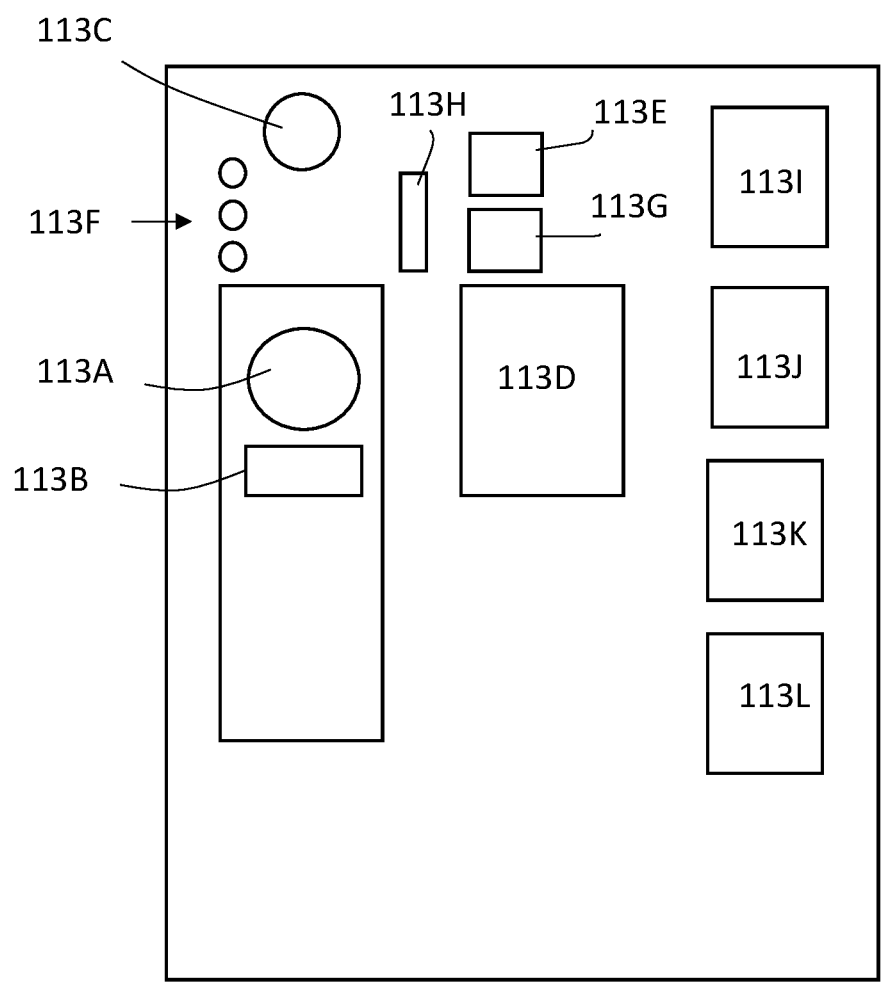
FIG. 8 is a schematic of an assay apparatus 102 configured to perform a plurality of different assays.

In another embodiment, identifiers 114 include indicia 114B printed on assay module 106 and/or assay device 104 (see FIG. 4A). In such embodiments, the means for decoding the identifier 114 can be embodied as a camera 113A (FIG. 8) configured to capture one or more images of the indicia 114B for assay identification. As shown in the schematic of FIG. 8, the camera 113A can have its own separate and dedicated circuit controlled by a device processor 113B within apparatus 102. Alternatively, camera 109I can be provided as a functional module 105 (see FIG. 3A) or can be by way of a smart device (e.g. smartphone 117 or tablet computer) (see FIG. 9A). Accordingly, referring collectively to FIGS. 1-10, a plurality of assay modules 106 can be adapted to fit a plurality of different assay devices 104 and fit in a same port 110, and by providing distinguishable indicia 114B that can be decoded by system 100, test device 104 can be identified for proper reading or analysis. In a variation of this approach, test device 104 includes printed indicia 114B, which can be captured by apparatus 102 or smartphone 117. Nonlimiting examples of indicia 114B include a barcode, a QR code, an alphanumeric code, and a color code.

In some embodiments, assay module 106 includes an RF tag 114C, and the apparatus 102 includes an RF tag electronic reader 113C. Accordingly, a plurality of assay modules 106 can be adapted to fit a plurality of different assay devices 104 and fit in a same port 110, yet be distinguished from one another by their corresponding RF tag 114C that can be detected by the apparatus 102, which informs the apparatus 102 the identity of the test device 104, and thus the type and sensitivity of the assay for proper reading and/or analysis.

In some embodiments, the system 100 uses two or more means for decoding identifiers 114. This approach can be preferred when a manufacturer offers different assays within a same cartridge footprint or when different manufacturers rely on a substantially similar cartridge footprint. In these instances, assay module 106, which is identified by a specific array of teeth 114A, can be paired with one or more assay device 104. Decoding the array of teeth 114A can be performed by photointerrupter 116 (FIG. 7), which can initiate a means for decoding a second identifier 114 (FIGS. 4A-4E), such as using a laser scanner or camera 113A to optically scan the assay device 104 for distinguishable indicia 114B (e.g. alphanumeric characters, colors, distinguishing surface characteristics, QR code) or using RF tag electronic reader 113C to read RC tag 114C. One of ordinary skill in the art will recognize that the means for decoding a secondary identifier 114 can also be used as a confirmation checkpoint, to confirm the assay device 104 prior to reading assay results.

In view of the above, the artisan will appreciate that identifiers 114 may be used to adjust apparatus 102 settings, assay identification, sample identification, patient identification, and others. Moreover, identifiers 114 can also be used to track patient or sample information throughout the testing and analysis process.

In addition to the above, assay modules 106 have been developed to address particular requirements for different assay devices 104. For example, returning to FIG. 4A, some assay devices 104 have elongated end portions 118, which in some embodiments can be a sample application pad. To account for this elongated portion 118, assay module 106 in FIG. 4A is slotted 120 so that elongated portion 118 can be bent and fed through slot 120. However, one challenge with bending portions of test device 104 is that in some instances, test device 104 applies a counter force. This counter force can potentially cause additional challenges in capturing test results. As such, an assay module 106 has been developed having at a slot 120 positioned transverse to the longitudinal extent of the assay module 106 for accepting and bending portions of a assay device 104 and a movable flap 121 configured to reversibly cover the slot 120 and extend parallel to the longitudinal extent of the module 106. This flap 121, when extending longitudinally, partially covers assay device 104 and provides a sufficient retaining force to prevent the assay device 104 from substantial movement, thereby permitting test results to be effectively captured.

Assay modules 106 have also been further improved for manipulation by users. For example, in FIG. 4E, assay module 106 has two separable parts, such as assay adapter 107A for holding assay device 104, and door 107B for receiving one or more assay adapters 107A. Assay module 106, at the proximal end of door 107B can include proximal knob 122 (see also FIG. 5C) and at the distal end of assay adapter 107A can include distal fingers slots 124 (see FIG. 4E). As such, the user can use knob 122 to assist with insertion or removal of assay module 106 to/from port 110; and finger slots 124 can assist the removal/insertion of assay adapter 107A when paired with door 107B.

In a related embodiment, door 107B holds an assay adapter 107A, which has a means for heating and/or cooling one or more assay devices 104 (e.g. a Peltier cooler or heater). In further embodiments, door 107B holds an assay adapter 117A configured as a heating and/or cooling block adapted to receive assay devices 104 configured as tubes or microtubes, which hold the sample for testing. In some embodiments the assay module 106 or assay adapter 107A includes a block for use as a thermocycler when inserted into apparatus 102 for conducting polymerase chain reaction (PCR) in assay devices 104 configured as microtubes. In other embodiments the assay module 106 or assay adapter 107A is configured for conducting isothermal amplification, including loop-mediated amplification (LAMP) and whole genome amplification (WGA), strand displacement amplification (SDA), helicase dependent amplification (HAD), recombinase polymerase amplification (RPA), nucleic acid sequences based amplification (NASBA), and others. In some embodiments, the door 117B holds a complete blood count (CBC) unit to measure the amount or concentration of white blood cells. The artisan will appreciate that door 107B may also house reagents for delivery to assay devices 104, such as through microfluidic or peristaltic pumps integrated into adapter 107A.

In some embodiments system 100 includes a stabilization structure, optionally configured as a gimbal, that improves stability of apparatus 102, assay module 106 and/or assay device 104 during shock or movement. In related embodiments, stabilization is accomplished electronically via a gravitational sensor that simultaneously sends position data to apparatus 102 so that image shaking can be corrected. In related embodiments, the stabilization is accomplished optically and/or electronically, such as by detecting positioning or movement of one or move bubble levelers or colored liquids/polymers that shift when moved in one or more directions, then adjusting for the movement. In some embodiments, apparatus 102 and/or assay module 106 further includes a shroud or shield configured to block ambient noise and/or interference, whether by caused by light, electrical signal, or magnetic forces. In some embodiments, there is a shroud configured to at least partially surround apparatus 102 to block noise and/or interference.

Among the further achievements, assay modules 106 have also been specifically developed for fluorescence assays. In particular, an assay module 106 has been developed, which includes an excitation light sources configured to deliver a wavelength to the assay device 104 that excites fluorescent molecules, which when coupled to an apparatus 102 that includes a fluorescence detector 113D, permits the use of fluorescent testing. In preferred embodiments, the excitation light source is one or more light emitting diodes (LEDs) 131. In exemplary embodiments, the LEDs 131 include one or more of an ultraviolet light, a violet light, a blue light, a green light, a yellow light, an orange light, and a red light, which are powered when inserted into apparatus 102. Bright field illumination can also be performed using a white light, such as using a white LED 133 included in an array of non-white LEDS or separately.

Turning now to the variety of assays that can be performed, the system 100 is configured to perform a variety of assays, which include, but are not limited to one or more of immunodiagnostic assays, lateral flow assays, DNA sequencing assays, bioluminescent assays, metabolic assays, cell proliferation assays, cell cytometry assays and others.

In some embodiments, the assay is one or more assay selected from the group consisting of a Sodium assay, Potassium assay, Chloride assay, BUN/Urea assay, Glucose assay, Hematocrit assay, Ionized Calcium assay, P02 assay, pH assay, PC02 assay, Creatinine assay, Lactate assay, Celite ACT assay, Prothrombin Time PT/INR assay, Kaolin ACT assay, Cardiac Troponin I/cTnI assay, Total Carbon Dioxide/TC02 assay, Creatine Kinase MB/CK-MB assay, B-Type Natriuretic Peptide/BNP assay, an immunodiagnostic assay, a DNA sequencing assay, a bioluminescent assay, a cell cytometry assay, a lateral flow assay, and an HbAlc assays.

Non-limiting examples of additional assays that can be carried out using the system 100 include detection of virus or antibodies against virus (e.g. severe acute respiratory syndrome (SARS); Covid-19), ABO Grouping (Blood Typing), Adrenocorticotropic Hormone level, Aldosterone level, Alpha 1 Antitrypsin level Alpha Fetoprotein level, Aluminum level, Amylase level, Antinuclear Antibody (ANA) Screen, Apolipoprotein Al (Apo Al) level, Arsenic level, B 12 level, Beta Carotene level, Beta HCG level, Bone-Specific Alkaline Phosphatase level, B-type natriuretic peptide level, Calcitonin, serum level, Calcium, Ionized level, Cancer Antigen 125 level, Cancer Antigen 15-3 level, Cancer antigen 27.29 level, Candida Antibodies level, Carbohydrate Antigen 19.9 level, Carcinoembryonic Antigen level Carnitine level, Catecholamine level, Celiac Disease Antibody Screen, Ceruloplasmin level, Chemistry Panel & Complete Blood Count (CBC), Chromium, plasma level, Chromogranin A level, Complement C3 level, Complement C4 level, Copper level, CoQIO (Coenzyme QIO) level, Cortisol level, Cortisol 24 Hour level, Cortisol AM/PM level, Coxsackie Group B Antibodies, C-Peptide level, C-Reactive Protein level, Creatine Kinase level, C-Telopeptide, serum level, Cystatin C level, Cytokine Panel level, Cytomegalovirus (CMV) Antibodies, IgG, Cytomegalovirus (CMV) Antibodies, IgM, D-Dimer level, Dehydroepiandrosterone Sulfate level, Dihydrotestosterone level, Epstein Barr Virus, ESR, Estradiol level, Total Estrogen level, Estrone level, F2-Isoprostane level, Factor VIII Activity, Ferritin level, Fibrinogen level, Folate level, Fructosamine level, Galectin-3 level, Gamma Glutamyl Transferase level, Glutathione level, Gluten level, Helocobacter Pylori, IgG, Hemoglobin AI C level, Hepatitis B surface Antibody, Hepatitis C Virus Antibody, Homocysteine level, Human Herpes Virus Antibodies, Insulin-Like Growth Factor Binding Protein 3 (IGFBP-3), Intact N-Terminal Propeptide of Type I Procollagen (PINP), Interleukin 6 (IL6), Interleukin 8 (IL-8), Interleukin Ibeta (IL-Ibeta), Iodine level, Ionized Calcium level, Iron & Total Iron-Binding Capacity (TIBC), Lactate Dehydrogenase (LD) Isoenzymes, Leptin level, Lipase level, Lipoprotein (a) level, Lithium level, Magnesium level, Mercury level, Myeloperoxidase level, Osteocalcin level, Parathyroid Hormone level, Reticulocyte Count, Serotonin level, Sex Hormone Binding Globulin level, Transferrin level, Troponin I level, Tumor Necrosis Factor—Alpha level, Vitamin A level, Vitamin B I level, Vitamin B 12 level, Vitamin B6 level, Vitamin C level, Vitamin D level, Vitamin K1 level, Zinc level, Adrenocorticotropic Hormone level, Alkaline Phosphatase level, Aluminum level, Ammonia level, Antidiuretic Hormone level, Antinuclear Antibody, Arsenic level, B Type Naturetic Peptide level, Total Estrogen level, Progesterone level, Testosterone level, Prostate Specific Antigen level (PSA), C-Reactive Protein (High Sensitivity-Cardiac) level, Cadmium level, Calcium, Ionized (Serum) Test, Candida Antigen I Antibody Profile, Ceruloplasmin levels, Chlamydia Pneunomonia level, Complete Metabolic Panel, Copper level, Cortisol level, C-Peptide level, Dehydroepiandrosterone level, Dihydrotestosterone level, Epstein-Barr Virus level, Erythrocyte Sedimentation Rate, Estradiol level, Estriol level, Estrone level, Ferritin level, Folate level, Follicle-Stimulating Hormone level, Luteinizing Hormone level, Glucose-6-Phosphate Dehydrogenase level, Glutathione level, Growth Hormone level, Hemoglobin Al e level, Homocysteine level, IgA Immunoglobin level, IgE Immunoglobin level, Insulin level, Insulin Growth Factor (IGF-1), Iron level, Lactic Acid Dehydrogenase level, Lead level, Leptin level, Lipid level, Magnesium level, Manganese, Methylmalonic Acid level, Microalbumin level, Parathyroid Hormone level, Prolactin level, Prothrombin Time (PT), Partial Thromboplastin (PTT) Prothrombin Time INR, Reverse Triiodothyronine level, Selenium level, Sex Hormone-Binding Globulin level, T-3 Uptake, Testosterone Free and Total, Thyroglobulin, Thyroid Antibody level, Thyroid Stimulating Hormone level, Thyroxine (T4), Thyroxine Binding Globulin level, Tumor Necrosis Factor-Alpha, Uric Acid level, Total Cholesterol, HDL Cholesterol level, LDL Cholesterol level, Urine Specific Gravity (SG), Urine pH, Urine Protein level, Urine Glucose level, Urine Ketones, Urine Blood (hemoglobin) and Myoglobin, Urine Leukocyte Esterase, Urine Nitrite, Urine Bilirubin, Urobilinogen, and Fecal Occult Blood.

In some embodiments, the immunodiagnostic assays are enzyme-linked immunosorbent assays (ELISA). The ELISA (sometimes also called an EIA) is a sensitive, inexpensive assay technique involving the use of antibodies (or other binding moieties) coupled to indicators (e.g. enzymes like horseradish peroxidase and alkaline phosphatase) used to detect the presence or amount of an analyte of interest. While there are several different types, basically ELISAs are created by coating a suitable plastic (the solid phase) with an antibody. To complete the reaction, a sample believed to contain the antigen of interest is added to the solid phase. Then a second antibody coupled with an enzyme is used followed by washing unbound secondary, then addition of a color-forming substrate for the enzyme. In some embodiments, the ELISA assay is based on comparison of color type, color intensity, or a combination thereof to one or more references. In some embodiments, the assay device 104 includes one or more wells in which the ELISA assay can be performed and the apparatus 102 includes an optical reader for reading colorimetric changes due to the ELISA reaction.

In some embodiments, the immunodiagnostic assays are lateral flow assays. Lateral flow tests also known as Lateral Flow Immunochromatographic Assays are simple devices intended to detect the presence (or absence) of a target analyte in sample (matrix) without the need for specialized and costly equipment, though many lab based applications exist that are supported by reading equipment. Typically, these assays are used for medical diagnostics either for home testing, point of care testing, or laboratory use. A widely spread and well-known application is the home pregnancy test. The lateral flow assay is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material that acts as a waste container (also called a "sink"). Lateral Flow Assays can operate as either competitive or sandwich assays. In some embodiments, the lateral flow assay based on comparison of line intensity, line color, or a combination thereof to one or more reference lines. There can also be sample and negative control lines. To this end, the assay device 104 can be a lateral flow test strip and results can be read optically using the apparatus 102, the color and intensity can be assessed, and the results displayed or transmitted as desired.

The systems and methods also include nucleic acid sequencing assays. In particular, an assay device 104 can be embodied as a DNA sequencing chip or a nucleic acid array that works with the apparatus 102 to conduct DNA sequencing analysis.

The systems and methods can also include metabolic assays and cell proliferation assays. In such embodiments, the assay device 104 can be configured as a container 105 with electrodes 119A-119B that sense changes in analyte concentration or pH, which is indicative of metabolism and thus cell growth (see FIG. 2C).

Non-limiting examples of bioluminescent (or chemiluminescent) assays performed fully or in part by the assay device 104 and optionally assay module 106 include luciferase assays. In biological research, luciferase is commonly used as a reporter to assess the transcriptional activity in cells that are transfected with a genetic construct containing the luciferase gene under the control of a promoter of interest. Additionally, proluminescent molecules that are converted to luciferin upon activity of a particular enzyme can be used to detect enzyme activity in coupled or two-step luciferase assays. Such substrates have been used to detect caspase activity and cytochrome P450 activity, among others.

Luciferase can also be used to detect the level of cellular ATP in cell viability assays or for kinase activity assays. Luciferase can act as an ATP sensor protein through biotinylation. Biotinylation will immobilize luciferase on the cell-surface by binding to a streptavidin-biotin complex. This allows luciferase to detect the efflux of ATP from the cell and will effectively display the real-time release of ATP through bioluminescence. Luciferase can additionally be made more sensitive for ATP detection by increasing the luminescence intensity through genetic modifications.

An example of a bioluminescence ATP assay is the ATP Bioluminescence Assay Kit CLS II by Roche Applied Science, which is specially developed for applications in which constant light signals are required for kinetic studies of enzymes and metabolic studies, or if coupled enzymatic assays are applied. If ATP determinations are manually started, the CLS Kit provides high reproducibility due to the constant signal generation. However, the sensitivity of the kit is lower by a factor of 10 as compared to the ATP Bioluminescence Assay Kit HS II, which is recommended for determinations in the high-sensitivity range. The ATP Bioluminescence Assay Kit HS II also contains an efficient cell lysis reagent and can be used for the detection of ATP in microorganisms or animal cells. The ATP Bioluminescence Assay Kit CLS II has a Detection limit of 10-11 M ATP (10-15 moles), using a luminometer.

In some embodiments, an assay module 106 is configured to perform a cell cytometry assay, and where the assay module 106 or apparatus 102 (see FIG. 8) includes a pump 113E, a laser diode 113F, a microcomputer 113G, and an optical sensor 113H. Cell cytometry is a laser-based biophysical technology employed in cell counting, cell sorting, biomarker detection and protein engineering, by suspending cells in a stream of fluid and passing them by an electronic detection apparatus. It allows simultaneous multiparametric analysis of the physical and chemical characteristics of up to thousands of particles per second. Flow cytometry is routinely used in the diagnosis of health disorders, especially blood cancers, but has many other applications in basic research, clinical practice and clinical trials. A common variation is to physically sort particles based on their properties, so as to purify populations of interest.

As a non-limiting example, a beam of light (usually laser light (e.g. laser diode 113F)) of a single wavelength is directed onto a hydrodynamically focused stream of liquid. A number of detectors (e.g. optical sensors 113H) are aimed at the point where the stream passes through the light beam: one in line with the light beam (Forward Scatter or FSC) and several perpendicular to it (Side Scatter or SSC) and one or more fluorescence detectors. Each suspended particle from 0.2 to 150 micrometers passing through the beam scatter the ray, and fluorescent chemicals found in the particle or attached to the particle may be excited into emitting light at a longer wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual particle. FSC correlates with the cell volume and SSC depends on the inner complexity of the particle (i.e., shape of the nucleus, the amount and type of cytoplasmic granules or the membrane roughness). This is because the light is scattered off of the internal components of the cell. Some flow cytometers on the market have eliminated the need for fluorescence and use only light scatter for measurement. Other flow cytometers form images of each cell's fluorescence, scattered light, and transmitted light.

Detection methodologies used by the apparatus 102 depend, at least in part, on the assay being performed. In some embodiments, the apparatus 102 includes an imaging module and/or detector that detects optical wavelengths. One of ordinary skill in the art will recognize that apparatus 102 can include imaging components, such as lenses (e.g. dichroic lens, half ball lens, concave lens, convex lenses, collimator), filters (e.g. bandpass filters), CCD sensors, CMOS sensors and the like to selectively collect wavelengths for testing. Further, the apparatus 102 can include character recognition software for decoding indicia 114B.

In some embodiments, the apparatus 102 detects colorimetric changes that occur in a cuvette 111B. As such, the apparatus 102 or assay module 106 may be configured to, for example, transmit a beam of energy (e.g. light, radiation) through the cuvette 111B where it may be detected by a detector (e.g. optical sensor 113H) within the apparatus 102. In some embodiments, the beam of light interacts with the cuvette 111B and the apparatus 102 uses Raman scattering to conduct the assay. In other embodiments, the beam of light interacts with the cuvette 111B and the apparatus 102 detects, measures or calculates light absorbance. In some embodiments the beam of energy is from an excitation light source configured to deliver a wavelength to the assay device 104 that excites one or more fluorescent molecules, such that a fluorescence detector within the apparatus 102 can detect fluorescence from the cuvette 111B.

In some embodiments, the apparatus 102 uses imaging to determine qualitatively or quantitatively the amount of analyte 103A-103D captured on a test strip 111A. To this end, FIGS. 4A-4E exemplify the nonlimiting diversity of test strips 111A that can be used with the assay modules 106.

In some embodiments, the apparatus 102 includes electronic components and circuitry, such as but not limited to a microprocessor 113I, memory 113J, and a transceiver 113K (or, alternatively, separate transmitter and receiver). In some embodiments, the microprocessors 113I are solo core, dual-core, quad-core, 8-core, 16-core, 32-core, 64-core microprocessors. The microprocessors 113I may be graphic processors with one core or more than one core. In some cases, the microprocessors 113I are microcontrollers and single processors. Alternatively, the microprocessor 113I may be an electronic circuitry designed specifically to process the data described in this subject matter. In addition, non-transitory memory includes software that is configured to cause the processor to carry out various processes described herein.

In some embodiments, the apparatus 102 includes one or more cameras 113A, detectors (e.g. electronic 113D, radiation), or other imaging modalities. Cameras 113A or detectors can be controlled by processors 113B. Alternatively, cameras 113A and detectors can be configured to transmit signals wirelessly, such as to smartphones 117, tablets and/or one or more single board computers 109J, such as but not limited to a Raspberry Pi, optionally running Lynux. In some embodiments, the apparatus 102 includes a luminescence recorder 113K (including chemiluminescence) adapted to record luminescence generated by the assay device 104 as it tests a sample using a luminescence technique. In some embodiments, the luminescence recorder 113K is selected from a camera, a fluorescent light recorder, a UV recorder, or combinations thereof. In some embodiments, the luminescence recorder is a built-in camera of a portable computing device. In some embodiment, the luminescence recorder includes a light source and a light receiver, such as a pin diode/amplifier type receiver tuned to a specific wavelength.

Figure 9A:
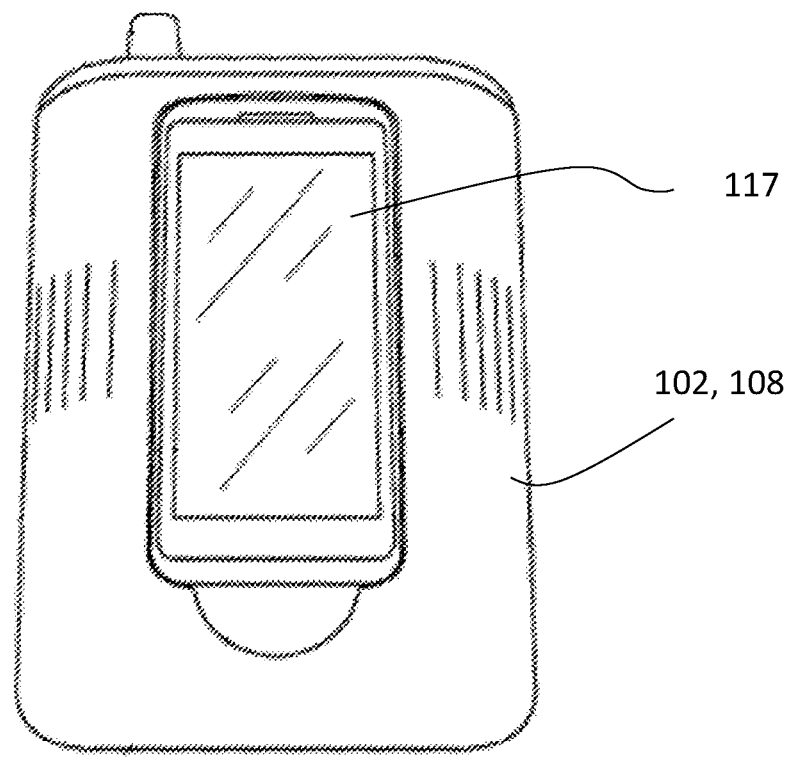
FIGS. 9A-9B depict an embodiment of an assay apparatus 102 that couples to a smartphone 117.
Figure 9B:
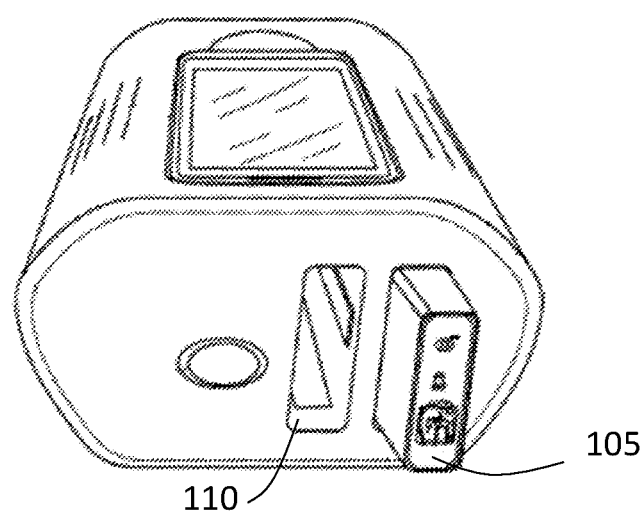

In some embodiments, the frame 108 is configured to operably couple with a smartphone 117, tablet or other computing device so that one or more of the electronic components of the computing device are utilized as the electronic components of the system 100. For example, as shown in FIGS. 9A-9B, some embodiments, the frame 108 is adapted to receive a smartphone 117 or computer tablet such that the smartphone 117 or tablet camera aligns with the assay device 104 to read assay results. In other embodiment, the apparatus 102, which may include an imaging circuit, a CCD sensor or CMOS sensor, is configured to couple with a computing device so that the computing device is operatively integrated with the apparatus 102 to collect and analyze the data. The imaging circuit can include a detection array. In some embodiments, the portable computing device is selected from a smartphone 117 or a tablet computer. In some embodiments, the computing device includes a downloadable software module configured to provide step-by-step guidance for coupling, collecting and analyzing data. In some embodiments, the computing device includes a downloadable software module configured to collect, process and organize data from the apparatus 102, assay device 104, assay module 106, or a combination thereof. In some embodiments, the computing device includes a downloadable software module configured to communicate data to a user, where the data is acquired from the assay module 106, the apparatus 102, or a combination thereof. In some embodiments, the assay information is securely communicated to the user through a server. In some embodiments, the server is an Internet server or a local access network server. In some embodiments, the user is a patient, a doctor, or a nurse. Computing devices suitable for use in the present disclosure include, but are not limited to, mobile phones, mobile computing devices, smartphones, portable computers, tablet computers, and mobile computers.

In some embodiments, images formed by individual cameras or other imaging modalities or detectors are assembled to create a single image with a wider field of view. In some embodiments, images formed create an image captured with natural light. The embodiments are to artificially increase the field of view with two cameras.

In still another improvement, stabilization has been improved such as to improve assay reading while the apparatus 102 undergoes shock. In some embodiments, the smartphones, tablets or optical processing includes optical stabilization software for stabilizing optical reading or results.

In some embodiments, the apparatus 102 includes a means for wireless communication configured to transfer data with a corresponding means for wireless communication on a module as would a mechanical coupler (e.g. a prong-based system). Non-limiting examples of wireless transmission technologies suitable for use as universal operable coupler in the apparatus 102 include 3G transceivers, 4G transceivers, 5G transceivers, Bluetooth transceivers, visible light signal transceivers, infrared transceivers, RF transceivers, and near field transceivers.

As previously described, the apparatus 102, in some embodiments, is configured to receive functional module 105 and/or assay module 102 within any one of its ports 110. In general, a functional module 105 provides a functionality without conducting a biological assay. For example, a functional module 105 may couple with the apparatus 102 by way of the port 110 and provide a reader, processor, or memory that is operably coupled with the electronics of apparatus 102. In some embodiments, one or more electronic components used by the apparatus 102 are within one or more functional modules 105, which are operational when plugged into the port 110. The functional module 105 can electrically connect one or more assay modules within the apparatus 102.

Returning again to FIG. 3A, in some embodiments, a functional module 105 includes one or more of the following functional devices: a battery 109A, a wired or wireless data transmission device 109B, a microprocessor 109C, a transitory memory device, a non-transitory memory device, an interface for receiving and recording signals from at least one vital sign detector 109D, a luminescence recorder 109E, a display device 109F, a portable computing device 109J (e.g. Raspberry Pi), a data storage device, an optical device, a motor, a tag, an RF tag, a sensor, a thermal sensor 109G, a speed sensor, a light sensor, an invisible light sensor, an electromagnetic wave sensor, an acoustic wave sensor, a transponder, a light source, an invisible light source, an electromagnetic wave source, a mechanical wave source, an acoustic wave source, a camera 109I or other imager, a pump, an actuator, and combinations thereof. A camera 109I or other imager as described herein may be precisely adjusted and controlled using software.

In some embodiments the functional module 105 increases the processing speed of sample data compared to the processor in the apparatus 102, then passes the processed answer to the apparatus 102 in order to more quickly process a sample or for other reasons. In other embodiments, a functional module 105 can simply hold a rechargeable battery 109A that can back-power the apparatus 102 for long periods of time.

In some embodiments, at least one functional module 105 includes a battery 109A, and where the apparatus 102 further includes a power inlet for receiving electric power from the battery 109A. In some embodiments, at least one functional module 105 includes an interface for at least one vital sign detector 109D operatively associated with functional module 105. In some embodiments, the at least one vital sign detector 109D collects body temperature, heart rate, blood pressure, respiratory rate, or combinations thereof. In some embodiments, the at least one functional module 105 includes a luminescence recorder 109E adapted to record luminescence generated by the assay device 104. In some embodiments, the luminescence recorder 109E is selected from a camera or other imager, a fluorescent light recorder, a UV recorder, a diode/amplifier type receiver, or combinations thereof. In some embodiments, the luminescence recorder is a built-in camera of a portable computing device.

In some embodiments, at least one functional module 105 includes a display 109F adapted to display assay module 106 derived data, functional module 105 derived data, sample related data, or combinations thereof. In some embodiments the display 109F is a high-resolution display 109F. In some embodiments, the high-resolution display 109F further includes a touch screen overlay. In some embodiments, the display is a display window of a portable computing device (not shown).

In some embodiments, at least one functional module 105 includes data storage 109H to store information received from the assay module 106, the functional module 105, or a combination thereof.

In some embodiments, at least two functional modules 105 have different shapes and the apparatus 102 has at least two ports 110 with different shapes to releasably retain the at least two differently shaped modules 105. In some cases, two or more functional modules 105 are physically connected through an electric wire, a tube, or an optical fiber. In some embodiments, two or more functional modules 105 are wirelessly coupled through a wireless communication.

As shown in FIGS. 9A-9B, it should be also be understood that one or more functional modules 105 and/or assay modules 106 are suitable for use with embodiments of the apparatus 102 that integrate with a computing device such as a smartphone 117. In these embodiments, a housing of apparatus 102 is configured to operably couple with a smartphone 117 or tablet as well as one or more assay modules 106 that couple with the apparatus 102 through one or more ports 110. In some embodiments, the portable computing device is coupled to at least one functional module 105 (see available port(s) 110 in FIG. 5C and FIG. 9B). In some embodiments, the portable computing device includes a software module configured to communicate data to a user, where the data is acquired from a functional module 105 and/or assay module 106 coupled with the housing of the apparatus 102. In some embodiments, the data is securely communicated to the user through a server. In some embodiments, the data is an Internet server or a local access network server. In some embodiments, the user is a patient, a doctor, a nurse, or a medical practitioner.

In some embodiments, the apparatus 102 includes connectors that mate with one or more complementary connectors (e.g. prongs 123 on functional modules 105 (see FIG. 3A)), assay modules 106, another assay apparatus 102, USB hubs, cabling, printed circuit assemblies, adapters and/or batteries. As will be described in passages that follow, in some embodiments, a same connector array connects to two or more functional modules 105 and/or assay modules 106.

As already introduced, the frame 108 is configured with at least one module port 110, which is an opening configured for interchanging one or more functional modules 105 or assay modules 106. In some embodiments, portable frame 108 is configured to receive two or more assay modules 106 simultaneously, preferably in different ports 110, but could be in a same port 110 (e.g. by inserting two assay adapters 107A into a single door 107B or two assay devices 104 into a single assay adapter 107A). Accordingly, in some embodiments a plurality of ports 110 are each sized to interchangeably receive at least one functional module 105 or assay module 106 at a time while in other embodiments, at least one port 110 is sized to receive two or more functional modules 105 and/or assay modules 106.

Ports 110 may also contain coupling components that provide for the removable coupling of functional and assay modules 105, 106 within port 110. Such removable coupling components can include male/female components, snap fit components, springs, and/or magnets. Port 110, in some embodiments, includes coupler that provides for operable coupling between apparatus 102 and functional module 105 and/or assay module 106. That is, port 110 can contain an operable coupler configured to connect to functional module 105 (e.g. prongs 123 in FIG. 3A) or assay module 106 within port 110 such that functional module 105 or assay module 106 functionally connects to apparatus's 102 electronic components including, referring now to FIG. 8, camera 113A, processor 113B, transceiver 113K, memory 113J, and/or battery. In some embodiments, the operable coupler includes conductive prongs on either a module (e.g. functional module 105, assay module 106) or within the port 110 to mate with corresponding prong receivers that electrically connect the functional module 105, assay module 106, and/or assay device 104 to the apparatus 102. In these embodiments, there is additional circuitry connecting the conductive operable coupler within the port 110 to the electronics and circuitry of the apparatus 102 so that electrical signals travel from the assay device 104 to the assay module 106, and through the port 110 of the frame 108, optionally into the electronics of the apparatus 102. It should be understood that other conductive mechanical coupling techniques are suitable or use with the apparatus 102 including any other means of creating a detachable, electrical or optical connection between a module within a port 110 and the port 110.

In some embodiments, one or more walls of port 110 are disposed on an adjustable track so that distances between walls at least partially defining the port 110 can be adjusted by making the overall size of enclosure of the port 110 smaller, larger or shaped differently. That is, fitting different sized functional modules 105 and assay modules 106 within an adjustable port 110 can be accomplished by making port 110 either larger or smaller in size. Similarly, port 110 may include one or more adjustable bars within port 110 that run the length, width, and/or depth of port 110 and when a bar is adjusted it effectively changes the depth, width and/or length of port 110.

Relatedly, in some embodiments, assay module 106 is configured with an interoperability feature such as adjustable wall(s), bar(s) or swing arm(s) configured to change dimensions of the assay module 106 for receiving different sized assay devices 104, such as different sized containers. In this way, an assay module 106 may be configured to receive assay devices 104 having different dimensions or may be configured to receive multiple assay devices 104 and/or samples at once.

Adjustable walls or bars, in some embodiments of apparatus 102 and assay module 106, include components that extend externally from apparatus 102 or assay module 106 and are attached to one or more adjustable walls or bars so that a user can manually adjust the position of the adjustable wall or bar by moving the externally extending component. In some embodiments, an adjustable wall or bar within apparatus 102 or assay module 106 is coupled to an actuator of the apparatus 102 or assay module 106 so that the adjustable wall or bar is moved automatically by the actuator, thereby resizing port 110 or opening in apparatus 102 or assay module 106 so that the size of the opening is adjusted. In some embodiments that include an actuator, the actuator is coupled with a sensor that senses at least one dimension of a component (e.g. a sample container) to be received within the apparatus 102 or assay module 106 and the actuator is configured to adjust at least one wall or bar within the apparatus 102 or assay module 106 in order to accommodate the component within apparatus 102 or assay module 106.

In some embodiments, the apparatus 102 is configured to receive multiple assay modules 106 and/or samples at once and run a number of different assays in parallel by running assays using one or more assay devices 104 and/or directly assaying a sample that is received by the apparatus 102. In some embodiments, two or more assay modules electrically connect to a functional module 105, for communication with the apparatus 102.

In some embodiments, a universal operability coupler is in general a mechanism for creating a coupling between a module 105, 106 and the apparatus 102 via the one or more ports 110. In some embodiments, a prong coupling system (as described above) within the port 110 is configured to receive or mate with corresponding prong receiver and/or prongs 123 (depending on whether the prongs 123 are within port 110 or positioned on a module 105, 106). For example, a prong receiver within a port 110 may be configured to receive (i.e. couple with) multiple prong 123 numbers and/or configurations. As a further example, a prong receiver may have six openings which will allow it to mate with one prong 123, two prongs 123, three prongs 123, four prongs 123, five prongs 123, or six prongs 123. Or alternatively, there may be multiple prongs 123 within a port 110 configured to mate with a prong receiver on a module (e.g. functional module 105 or assay module 106) and one or more of the prongs 123 may be retractable so that the prongs 123 within a port 110 can be adjusted to mate with a prong receiver having different numbers of openings. As a further example, a port 110 may have a universal operable coupler within it having six retractable prongs 123 configured to mate with a prong receiver on a functional module 105 or an assay module 106 (or assay device 104) having one hole (i.e. and five prongs 123 are retracted), two holes (i.e. and four prongs 123 are retracted), three holes (i.e. and three prongs 123 are retracted), four holes (i.e. and two prongs 123 are retracted), five holes (i.e. and one prong 123 is retracted) or six holes (i.e. and no prongs 123 are retracted). Further, in the example of the prong coupling system, as explained, an electrical connection can be created between the apparatus 102 and the module 105, 106 when the prongs 123 and prong receiver are mated (i.e. coupled). This electrical connection provides for the one directional or bi-directional transfer of data between the apparatus 102 and the module 105, 106. The adjustability of the prong system in this embodiment, makes it a universal coupler so that no matter what the prong or prong receiver configuration on any module 105, 106, the module 105, 106 can operatively couple with the apparatus 102. Likewise, by providing a retractable prong system, the assay module 106 can inform the apparatus 102 the identity of the assay device 104 and thus instruct the apparatus 102 to perform the proper assay. Likewise, by providing a retractable prong system for interacting with a different array of prongs, the functional module 105 can inform the apparatus 102 the identity of the functional module 105 and thus instruct the apparatus 102 accordingly.

In some embodiments, the apparatus 102 also includes one or more non-modular components configured to carry out one or more assays. In these embodiments, the non-modular component is affixed to or integrated with the apparatus 102. For example, an apparatus 102 in some embodiments includes an opening or port 110 configured to directly receive a sample or a container of a sample such as, for example, a cartridge, test strip 111A, or cuvette 111B. As described, the container, in some embodiments, includes components configured to analyze the sample within the container. Examples of such components may include electrical sensors such as those that measure pH or metabolites released from microorganisms. Thus, in some embodiments, the apparatus 102 includes at least one module that is permanently affixed to or integrated with the frame 108 of the apparatus 102. That is, in this embodiment, not all modules are removable from the apparatus 102.

Retuning to FIGS. 1-10 collectively again, a system 100 as described herein, includes an apparatus 102 (or any embodiment of the apparatus) along with a third-party module, where the third-party module includes any module that was not originally manufactured with apparatus 102 and utilizes one or more interoperability mechanisms to couple with the apparatus 102.

The system 100 as described herein, in some embodiments, includes an apparatus 102 integrated with a computing device such as a smartphone 117. As previously described, in these embodiments, frame 108 of an apparatus 102 is configured to operably couple with a smartphone as well as one or more functional modules 105 and/or assay modules 106 that couple with the apparatus 102 through one or more ports 110.

The system 100 as described herein, in some embodiments, includes one or more assay modules 106 configured to receive and analyze a sample or receive data from a container or third party module that contains a sample. In these embodiments, the assay module 106 is configured to transmit data through a wired or wireless transmission to a network, remote server, or computing device.

In some embodiments, a system includes connectivity to the Cloud or a remote server, wherein data is aggregated and, in some embodiments, analyzed further as described herein.

Figure 10:
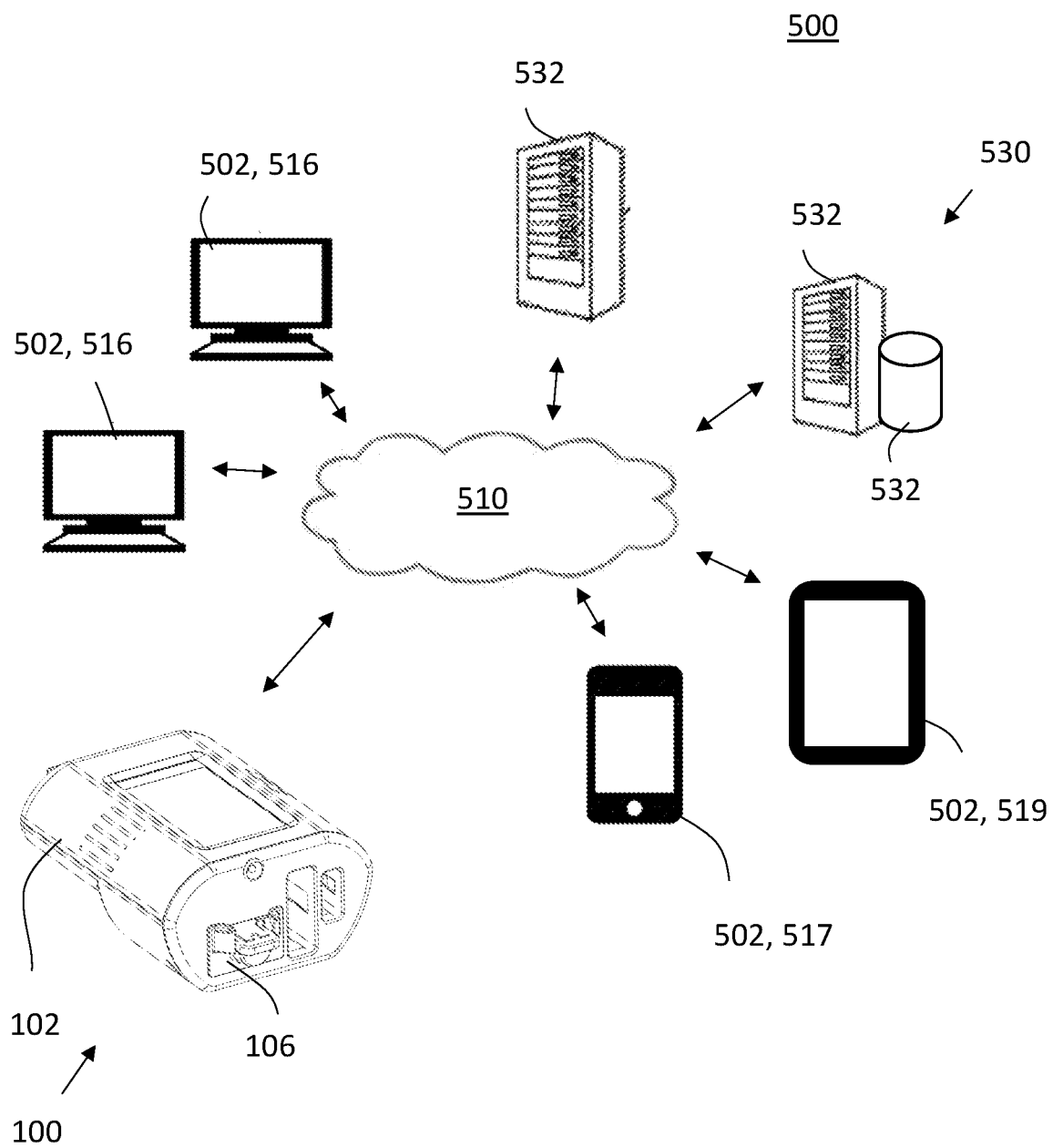
FIG. 10 shows an example of environment 500 that can be employed to interact with the testing system.

In particular, FIG. 10 shows an example of an environment 500 that can be employed to execute implementations of one or more embodiments of the system 100. An exemplary platform includes computing devices 502, modular hand-held point of care system 100, a back-end system 530, and a network 510. In some embodiments, there are possibilities of connecting Peer-to-peer. For example, in some embodiments, there is a satellite link that communicates with the apparatus 102 using a functional module 105 (see FIG. 3A). The satellite link may or may not connect to the internet, so this would be Peer-to-Peer. Test result data can be saved by many point of care tests and uploaded to the Internet as aggregated data. This aggregated data can be from a single apparatus 102 or be a combination of data received from one or more external devices together with results from the apparatus 102.

In some embodiments, the network 510 includes a local area network (LAN), wide area network (WAN), the Internet, or a combination thereof, and connects web sites, devices (e.g., the computing devices 502, smartphones 517 and the medical device or system 100) and back-end systems (e.g., the back-end system 530). In some embodiments, the network 510 can be accessed over a wired and/or a wireless communications link. For example, mobile computing devices (e.g., the smartphone 517 and the tablet device 519), can use a cellular network to access the network 510. In some embodiments, the users include physicians, patients, network technicians including network administrators and authorized programmers, nurses, residents, hospital administrators, insurers, and any other healthcare provider.

In the depicted example, the back-end system 530 includes at least one server system 532 and a data store 534. In some embodiments, the at least one server system 532 hosts one or more computer-implemented services and portals employed within the described platform such that users can interact with using the respective computing device 502. For example, computing devices 502 may be used by respective users to generate and retrieve reports regarding patient data and test results taken by the system 100 through services hosted by back-end system 530. In some embodiments, back-end system 530 provides an API service with which the server 532 may communicate.

In some embodiments, back-end system 530 includes server-class hardware type devices. In some embodiments, back-end system 530 includes computer systems using clustered computers and components to act as a single pool of seamless resources when accessed through network 510. For example, such embodiments may be used in data center, cloud computing, storage area network (SAN), and network attached storage (NAS) applications. In some embodiments, back-end system 530 is deployed using a virtual machine(s).

In some embodiments, computing devices 502 include any appropriate type of computing device, such as a desktop computer 516, a laptop computer, a handheld computer, a tablet computer 519, a personal digital assistant (PDA), a network appliance, a camera or other imager, a smartphone 517, an enhanced general packet radio service (EGPRS) mobile phone, a media player, a navigation device, an email device, a game console, or an appropriate combination of any two or more of these devices or other data processing devices. In the depicted example, the computing device 502 is a smartphone 517, the computing device 502 is a desktop computing device 516, and the computing device 502 is a tablet-computing device 519. In some embodiments, the server computing device 532 includes any appropriate type of computing device, such as described above for computing devices 502 as well as computing devices with server-class hardware. In some embodiments, the server computing device 532 includes computer systems using clustered computers and components to act as a single pool of seamless resources. It is contemplated, however, that implementations of the present disclosure can be realized with any of the appropriate computing devices, such as those mentioned previously.

In some embodiments, data that is received from one or more apparatuses 102 and/or assay modules 106 as described herein is aggregated and wirelessly transmitted to or received from a remote server 532 (e.g. the Cloud) where data from multiple sources is stored. For example, data from multiple apparatuses 102 and/or assay modules 106 may be aggregated for the purpose of quality control or performance monitoring. For example, data from multiple apparatuses 102 and/or assay modules 106 may be aggregated for the purpose of patient study. For example, data from an apparatus 102 and/or assay module 106 relating to one or more samples from a patient may be aggregated with other patient data including physiologic data (e.g. from a monitoring device) and/or patient medical record data.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A modular hand-held point of care testing system, comprising:
   (a) a plurality of different assay adapters configured to receive a plurality of different assay devices that perform assays on one or more samples;
   (b) a shared door that that interchangeably receives the plurality of different assay adapters, wherein at least two of the plurality of assay adapters or at least two of the assay devices comprise different identifiers that distinguish the assays from each other, wherein at a distal end of at least one assay adapter are finger slots for removing a received assay adapter from the door and a proximal end of the door comprises a handle for removing the assay module from the frame;
   (c) an apparatus comprising a portable frame configured to interchangeably receive the shared door and a means for decoding the different identifiers when received by the frame; and
   (d) a means for reading assay results.

2. The system of claim 1, wherein the different identifiers are differently ordered teeth and the means for decoding the different identifiers is a photointerrupter.

3. The system of claim 1, wherein the different identifiers comprise RFID or NFC circuits, further wherein the means for decoding the different identifiers comprises a corresponding RFID or NFC reader.

4. The system of claim 1, wherein the different identifiers comprise different indicia, selected from the group consisting of a bar code, a QR code, and an alphanumeric code, further wherein the means for decoding the different identifiers comprises a camera or optical scanner.

5. The system of claim 1, wherein the means for decoding the different identifiers comprises an imaging module with a camera circuit for optically capturing the different identifiers and assay results.

6. The system of claim 1, wherein at a distal end of at least one assay adapter is a slot positioned transverse to it's longitudinal extent and a movable flap that extends parallel over the slot.

7. The system of claim 1, wherein at least one assay is a lateral flow assay providing assay results by line intensity or line color.

8. The system of claim 1, further comprising a bright field light source or an excitation light source configured to deliver a wavelength to the received assay device that excites fluorescent molecules, and a fluorescence detector for detecting fluorescence.

9. The system of claim 1, further comprising a functional module that performs an electrical operation to supplement the testing system.

10. The system of claim 9, wherein the functional module is configured for interchangeable insertion into the same port as the door.

11. The system of claim 9, wherein the functional module is selected from the group consisting of a battery, a wireless data transmission device, a wired data transmission device, a microprocessor, an interface for receiving and recording signals from at least one vital sign detector, a luminescence recorder, a display device, a portable computing device, and a data storage device.

12. A modular hand-held point of care testing system, comprising:
  (a) a plurality of different assay adapters configured to receive a plurality of different assay devices that perform assays on one or more samples;
  (b) a shared door that that interchangeably receives the plurality of different assay adapters, wherein at least two of the plurality of assay adapters or at least two of the assay devices comprise different identifiers that distinguish the assays from each other, wherein the different identifiers are differently ordered teeth and the means for decoding the different identifiers is a photointerrupter;
  (c) an apparatus comprising a portable frame configured to interchangeably receive the shared door and a means for decoding the different identifiers when received by the frame; and
  (d) a means for reading assay results.

13. A modular hand-held point of care testing system, comprising:
  (a) a plurality of different assay adapters configured to receive a plurality of different assay devices that perform assays on one or more samples;
  (b) a shared door that that interchangeably receives the plurality of different assay adapters, wherein at least two of the plurality of assay adapters or at least two of the assay devices comprise different identifiers that distinguish the assays from each other;
  (c) an apparatus comprising a portable frame configured to interchangeably receive the shared door and a means for decoding the different identifiers when received by the frame;
  (d) a means for reading assay results; and
  (e) a functional module that performs an electrical operation to supplement the testing system, wherein the functional module is configured for interchangeable insertion into the same port as the door.

* * * * *